US010525272B2

United States Patent
Thompson-Nauman et al.

(10) Patent No.: US 10,525,272 B2
(45) Date of Patent: Jan. 7, 2020

(54) IMPLANTABLE MEDICAL DEVICE SYSTEM HAVING IMPLANTABLE CARDIOVERTER-DEFIBRILLATOR (ICD) SYSTEM AND SUBSTERNAL LEADLESS PACING DEVICE

(71) Applicant: Medtronic, Inc., Minneapolis, MN (US)

(72) Inventors: Amy E. Thompson-Nauman, Ham Lake, MN (US); Melissa G. T. Christie, Ham Lake, MN (US); Paul J. DeGroot, Shoreview, MN (US); Rick D. McVenes, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/661,365

(22) Filed: Jul. 27, 2017

(65) Prior Publication Data
US 2017/0319863 A1 Nov. 9, 2017

Related U.S. Application Data

(62) Division of application No. 14/261,460, filed on Apr. 25, 2014, now Pat. No. 9,717,923.
(Continued)

(51) Int. Cl.
*A61N 1/39* (2006.01)
*A61N 1/375* (2006.01)
(Continued)

(52) U.S. Cl.
CPC .......... *A61N 1/3918* (2013.01); *A61N 1/362* (2013.01); *A61N 1/375* (2013.01);
(Continued)

(58) Field of Classification Search
CPC ....... A61N 1/3962; A61N 1/05; A61N 1/3956
See application file for complete search history.

(56) References Cited

U.S. PATENT DOCUMENTS

| 4,030,509 A | 6/1977 | Heilman et al. |
| 4,146,037 A | 3/1979 | Flynn et al. |
(Continued)

FOREIGN PATENT DOCUMENTS

| CN | 1859870 A | 11/2006 |
| CN | 102858403 A | 1/2013 |
(Continued)

OTHER PUBLICATIONS

Final Office Action from U.S. Appl. No. 14/261,479, dated Jul. 13, 2018, 9 pp.
(Continued)

*Primary Examiner* — Mark Bockelman
(74) *Attorney, Agent, or Firm* — Shumaker & Sieffert, P.A.

(57) ABSTRACT

Implantable cardiac systems and methods for providing substernal pacing in an ICD system are described. In one example, an implantable cardiac system comprises an ICD system and an implantable leadless pacing device (LPD) communicatively coupled to the ICD system. The ICD system includes an ICD and an implantable defibrillation lead having a proximal portion coupled to the ICD and a distal portion having a defibrillation electrode configured to deliver a defibrillation shock to a heart of the patient. The LPD includes a housing, a first electrode on the housing, a second electrode on the housing, and a pulse generator within the housing and electrically coupled to the first electrode and the second electrode. The housing of the LPD is implanted substantially within an anterior mediastinum of
(Continued)

the patient and the pulse generator is configured to deliver pacing pulses to a heart via the first and second electrodes.

13 Claims, 9 Drawing Sheets

Related U.S. Application Data

(60) Provisional application No. 61/819,946, filed on May 6, 2013.

(51) Int. Cl.
*A61N 1/362* (2006.01)
*A61N 1/372* (2006.01)

(52) U.S. Cl.
CPC ........... *A61N 1/37288* (2013.01); *A61N 1/39* (2013.01); *A61N 1/3962* (2013.01)

(56) References Cited

U.S. PATENT DOCUMENTS

| | | |
|---|---|---|
| 4,270,549 A | 6/1981 | Heilman |
| 4,280,510 A | 7/1981 | O'Neill |
| 4,291,707 A | 9/1981 | Heilman et al. |
| 4,437,475 A | 3/1984 | White |
| 4,512,351 A | 4/1985 | Pohndorf |
| 4,538,624 A | 9/1985 | Tarjan |
| 4,708,145 A | 11/1987 | Tacker, Jr. et al. |
| 4,765,341 A | 8/1988 | Mower et al. |
| 4,787,389 A | 11/1988 | Tarjan |
| 4,832,687 A | 5/1989 | Smith, III |
| 4,865,037 A | 9/1989 | Chin et al. |
| 5,036,854 A | 8/1991 | Schollmeyer et al. |
| 5,099,838 A | 3/1992 | Bardy |
| 5,125,904 A | 6/1992 | Lee |
| 5,176,135 A | 1/1993 | Fain et al. |
| 5,203,348 A | 4/1993 | Dahl et al. |
| 5,193,540 A | 5/1993 | Schulman |
| 5,255,691 A | 10/1993 | Otten |
| 5,255,692 A | 10/1993 | Neubauer et al. |
| 5,273,053 A | 12/1993 | Pohndorf |
| 5,292,338 A | 3/1994 | Bardy |
| 5,300,106 A | 4/1994 | Dahl et al. |
| 5,312,355 A | 5/1994 | Lee |
| 5,439,484 A | 8/1995 | Mehra |
| 5,441,504 A | 8/1995 | Pohndorf et al. |
| 5,456,699 A | 10/1995 | Armstrong |
| 5,476,493 A | 12/1995 | Muff |
| 5,509,924 A | 4/1996 | Paspa et al. |
| 5,534,018 A | 7/1996 | Wahlstrand et al. |
| 5,613,953 A | 3/1997 | Pohndorf |
| 5,690,648 A | 11/1997 | Fogarty et al. |
| 5,721,597 A | 2/1998 | Kakinuma et al. |
| 5,800,465 A | 9/1998 | Thompson et al. |
| 5,944,732 A | 8/1999 | Raulerson et al. |
| 5,951,518 A | 9/1999 | Licata et al. |
| 6,032,079 A | 2/2000 | KenKnight et al. |
| 6,059,750 A | 5/2000 | Fogarty et al. |
| 6,104,957 A | 8/2000 | Alo et al. |
| 6,120,431 A * | 9/2000 | Magovern ........... A61M 1/1068 600/17 |
| 6,122,552 A | 9/2000 | Tockman et al. |
| 6,159,198 A | 12/2000 | Gardeski et al. |
| 6,228,052 B1 | 5/2001 | Pohndorf |
| 6,324,414 B1 | 11/2001 | Gibbons et al. |
| 6,415,187 B1 | 7/2002 | Kuzma et al. |
| 6,445,954 B1 | 9/2002 | Olive et al. |
| 6,544,247 B1 | 4/2003 | Gardeski et al. |
| 6,721,597 B1 | 4/2004 | Bardy et al. |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,856,835 B2 | 2/2005 | Bardy et al. |
| 6,866,044 B2 | 3/2005 | Bardy et al. |
| 6,868,291 B1 | 3/2005 | Bonner et al. |
| 6,887,229 B1 | 5/2005 | Kurth |
| 6,890,295 B2 | 5/2005 | Michels et al. |
| 6,999,819 B2 | 2/2006 | Swoyer et al. |
| 7,033,326 B1 | 4/2006 | Pianca et al. |
| 7,050,851 B2 | 5/2006 | Plombon et al. |
| 7,069,083 B2 | 6/2006 | Finch et al. |
| 7,096,064 B2 | 8/2006 | Deno et al. |
| 7,117,039 B2 | 10/2006 | Manning et al. |
| 7,195,637 B2 | 3/2007 | Mika |
| 7,218,970 B2 | 5/2007 | Ley et al. |
| 7,225,034 B2 | 5/2007 | Ries et al. |
| 7,229,450 B1 | 6/2007 | Chitre et al. |
| 7,272,448 B1 | 9/2007 | Morgan et al. |
| 7,288,096 B2 | 10/2007 | Chin |
| 7,316,667 B2 | 1/2008 | Lindstrom et al. |
| 7,322,960 B2 | 1/2008 | Yamamoto et al. |
| 7,369,899 B2 | 5/2008 | Malinowski et al. |
| 7,389,134 B1 | 6/2008 | Karicherla et al. |
| 7,392,085 B2 | 6/2008 | Warren et al. |
| 7,450,997 B1 | 11/2008 | Pianca et al. |
| 7,496,408 B2 | 2/2009 | Ghanem et al. |
| 7,499,758 B2 | 3/2009 | Cates et al. |
| 7,539,542 B1 | 5/2009 | Malinowski |
| 7,627,375 B2 | 12/2009 | Bardy et al. |
| 7,655,014 B2 | 2/2010 | Ko et al. |
| 7,684,864 B2 | 3/2010 | Olson et al. |
| 7,736,330 B2 | 6/2010 | Bardy |
| 7,761,150 B2 | 7/2010 | Ghanem et al. |
| 7,765,014 B2 | 7/2010 | Eversull et al. |
| 7,801,622 B2 | 9/2010 | Camps et al. |
| 7,837,671 B2 | 11/2010 | Eversull et al. |
| 7,846,088 B2 | 12/2010 | Ness |
| 7,850,610 B2 | 12/2010 | Ferek-Petric |
| 7,890,191 B2 | 2/2011 | Rutten et al. |
| 7,908,015 B2 | 3/2011 | Lazeroms et al. |
| 7,920,915 B2 | 4/2011 | Mann et al. |
| 7,930,028 B2 | 4/2011 | Lang et al. |
| 7,930,040 B1 | 4/2011 | Kelsch et al. |
| 7,983,765 B1 | 7/2011 | Doan et al. |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,165,696 B2 | 4/2012 | McClure et al. |
| 8,260,436 B2 | 9/2012 | Gerber et al. |
| 8,280,527 B2 | 10/2012 | Eckerdal et al. |
| 8,340,779 B2 | 12/2012 | Harris et al. |
| 8,355,786 B2 | 1/2013 | Malinowski |
| 8,386,052 B2 | 2/2013 | Harris et al. |
| 8,394,079 B2 | 3/2013 | Drake et al. |
| 8,435,208 B2 | 5/2013 | Bardy |
| 8,442,620 B2 | 5/2013 | Silipo et al. |
| 8,452,421 B2 | 5/2013 | Thenuwara et al. |
| 8,478,424 B2 | 7/2013 | Tronnes |
| 8,478,426 B2 | 7/2013 | Barker |
| 8,594,809 B2 | 11/2013 | Yang |
| 8,886,311 B2 | 11/2014 | Anderson et al. |
| 9,126,031 B2 | 9/2015 | Tekmen et al. |
| 2002/0049476 A1 | 4/2002 | Bardy et al. |
| 2002/0120294 A1 | 8/2002 | Kroll |
| 2003/0088278 A1 | 5/2003 | Bardy et al. |
| 2003/0114908 A1 | 6/2003 | Flach |
| 2004/0059348 A1 | 3/2004 | Geske et al. |
| 2004/0102829 A1 | 5/2004 | Bonner et al. |
| 2004/0210293 A1 | 10/2004 | Bardy et al. |
| 2004/0215240 A1 | 10/2004 | Lovett et al. |
| 2004/0215308 A1 | 10/2004 | Bardy et al. |
| 2004/0230279 A1 | 11/2004 | Cates et al. |
| 2004/0230280 A1 | 11/2004 | Cates et al. |
| 2004/0230281 A1 | 11/2004 | Heil et al. |
| 2004/0230282 A1 | 11/2004 | Cates et al. |
| 2004/0236396 A1 | 11/2004 | Coe et al. |

(56) References Cited

U.S. PATENT DOCUMENTS

| | | |
|---|---|---|
| 2005/0049663 A1 | 3/2005 | Harris et al. |
| 2005/0131505 A1 | 6/2005 | Yokoyama |
| 2005/0277990 A1 | 12/2005 | Ostroff et al. |
| 2005/0288758 A1 | 12/2005 | Jones et al. |
| 2006/0041295 A1 | 2/2006 | Osypka |
| 2006/0116746 A1 | 6/2006 | Chin |
| 2006/0122676 A1 | 6/2006 | Ko et al. |
| 2006/0136004 A1 | 6/2006 | Cowan et al. |
| 2006/0161205 A1 | 7/2006 | Mitrani et al. |
| 2006/0247753 A1 | 11/2006 | Wenger et al. |
| 2006/0253181 A1 | 11/2006 | Schulman et al. |
| 2006/0265018 A1 | 11/2006 | Smith et al. |
| 2007/0023947 A1 | 2/2007 | Ludwig et al. |
| 2007/0049975 A1 | 3/2007 | Cates et al. |
| 2007/0088394 A1 | 4/2007 | Jacobson |
| 2007/0100409 A1 | 5/2007 | Worley et al. |
| 2007/0179388 A1 | 8/2007 | Larik et al. |
| 2007/0208402 A1 | 9/2007 | Helland et al. |
| 2007/0249992 A1 | 10/2007 | Bardy |
| 2008/0046056 A1 | 2/2008 | O'Connor |
| 2008/0243219 A1 | 10/2008 | Malinowski et al. |
| 2008/0269716 A1 | 10/2008 | Bonde et al. |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2009/0270962 A1 | 10/2009 | Yang et al. |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0042108 A1 | 2/2010 | Hibino |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0152798 A1 | 6/2010 | Sanghera et al. |
| 2010/0211064 A1 | 8/2010 | Mahapatra et al. |
| 2010/0217298 A1 | 8/2010 | Bardy |
| 2010/0217301 A1 | 8/2010 | Bardy |
| 2010/0241185 A1 | 9/2010 | Mahapatra et al. |
| 2010/0249696 A1 | 9/2010 | Bardy |
| 2010/0305428 A1 | 12/2010 | Bonner et al. |
| 2010/0318098 A1 | 12/2010 | Lund et al. |
| 2011/0009933 A1 | 1/2011 | Barker |
| 2011/0077708 A1 | 3/2011 | Ostroff |
| 2011/0125163 A1 | 5/2011 | Rutten et al. |
| 2011/0224680 A1 | 9/2011 | Barker |
| 2011/0224681 A1 | 9/2011 | Barker |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0123496 A1 | 5/2012 | Schotzko et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2012/0220849 A1 | 8/2012 | Brockway et al. |
| 2012/0316613 A1 | 12/2012 | Keefe et al. |
| 2013/0041345 A1 | 2/2013 | Kilcoin et al. |
| 2013/0103049 A1 | 4/2013 | Bonde |
| 2013/0158564 A1 | 6/2013 | Harris et al. |
| 2013/0238067 A1 | 9/2013 | Baudino |
| 2014/0330325 A1 | 11/2014 | Thompson-Nauman et al. |
| 2014/0330326 A1 | 11/2014 | Thompson-Nauman et al. |
| 2014/0330327 A1 | 11/2014 | Thompson-Nauman et al. |
| 2014/0330329 A1 | 11/2014 | Thompson-Nauman et al. |
| 2014/0330331 A1 | 11/2014 | Thompson-Nauman et al. |

FOREIGN PATENT DOCUMENTS

| | | |
|---|---|---|
| EP | 1541191 A1 | 6/2005 |
| JP | 2007500549 A | 1/2007 |
| WO | 2001023035 A1 | 4/2001 |
| WO | 0226315 A1 | 4/2002 |
| WO | 2004073506 A2 | 9/2004 |
| WO | 2005011809 A2 | 2/2005 |
| WO | 20100047893 A1 | 4/2010 |

OTHER PUBLICATIONS

Thompson-Nauman et al., "Implantable Cardioverter-Defibrillator (ICD) System Including Substernal Lead", JP Patent Application No. 2016-512987, Japanese Office Action dated Feb. 2, 2018, 4 pages.

"SQ-RX Pulse Generator, A Component of the S-ICD System, User's Manual, Model 1010," Cameron Health, Inc., Dec. 2, 2008, 46 pp.

Erickson, MD., "Non-thoracotomy ICD Implantation in Pediatric and Adult Congenital Heart Disease Patients," Oct. 2015, 44 slides.

Sgoifo et al., "Electrode Positioning for Reliable Telemetry ECG Recordings During Social Stress in Unrestrained Rats," Physiology and Behaviors, vol. 60, issue 6, Dec. 1996, pp. 1397-1401.

(PCT/US2014/036878) PCT Notification of Transmittal of the International Search Report and the Written Opinion of the International Searching Authority, dated Aug. 7, 2014, 8 pages.

Advisory Action from U.S. Appl. No. 14/261,470, dated Jan. 12, 2018, 3 pp.

Response to Office Action dated Oct. 12, 2017, from U.S. Appl. No. 14/261,479, filed Feb. 12, 2018, 19 pp.

Office Action from U.S. Appl. No. 14/261,488, dated Jan. 30, 2018, 10 pp.

Office Action from U.S. Appl. No. 14/261,456, dated Mar. 9, 2018, 7 pp.

Office Action from U.S. Appl. No. 14/261,470, dated Mar. 26, 2018, 10 pp.

Response to Office Action dated Jan. 30, 2018, from U.S. Appl. No. 14/261,488, filed Apr. 30, 2018, 12 pp.

Response to Office Action dated Mar. 26, 2018, from U.S. Appl. No. 14/261,470, filed Jun. 26, 2018, 18 pp.

Response to Office Action dated Mar. 9, 2018, from U.S. Appl. No. 14/261,456, filed Jun. 4, 2018, 15 pp.

Final Rejection from U.S. Appl. No. 14/261,488, dated Sep. 21, 2018, 14 pp.

Final Rejection from U.S. Appl. No. 14/261,479, dated Jul. 13, 2018, 9 pp.

Office Action from U.S. Appl. No. 14/261,479, dated Sep. 12, 2018, 17 pp.

Obadia, et al., "New Approach for Implantation of Automatic Defibrillators Using Videothoracoscopy", Journal Ann Cardiol Angeiol (Paris); Sep. 1994; 43 (7) Abstract Only, 1 page.

Lemmer, "Defibrillator Patch Constriction, Letter to the Editor", The Annals of Thoracic Surgery, 1996, 1 page.

Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.

Damiano, "Implantation of Cardioverter Defibrillators in the Post-Sternotomy Patient", The Annals of Thoracic Surgery, 1992; 53: pp. 978-983.

Piccione, et al., "Erosion of Extrapericardial Implantable Cardioverter Defibrillator Patch Through the Gastic Fundus with Fistulous Tract Information", Cardiology in Review; 2006; 14, e21-e23 pages.

Vyhmeister et al., "Simple Approach for Extrapericardial Placement of Defibrillator Patches via Median Sternotomy", The Annals of Thoracic Surgery; 1994; 57: 4 pages.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

(56) References Cited

OTHER PUBLICATIONS

Obadia et al., "Thoracoscopic Approach to Implantable Cardioverter Defibrillator Patch Electrode Implantation", Pacing and Clinical Electrophysiology; Jun. 1996; vol. 19; 6 pages.
Shapira, et al., "A Simplied Method for Implantation of Automatic Cardioverter Defibrillator in Patients with Previous Cardiac Surgery", Pacing and Clinical Electrophysiology, January Part I, 1993, vol. 16; 6 pages.
Quigley et al., "Migration of an Automatic Implantable Cardioverter-Defibrillator Patch Causing Massive Hemothorax", Journal Texas Heart Institute, Nov. 1, 1996; vol. 23, 4 pages.
Karwande et al., "Bilateral Anterior Thoracotomy for Automatic Implantable Cardioverter Defibrillator Placement in Patients with Previous Sternotomy", The Annals of Thoracic Surgery; Oct. 1992; 54(4); 3 pages.
Bielefeld et al., "Thoracoscopic Placement of Implantable Cardioverter-Defibrillator Patch Leads in Sheep", Circulation; Nov. 1993, vol. 88, No. 5, Part 2; 5 pages.
Frame et al., "Long-Term Stability of Defibrillation Thresholds with Intrapericardial Defibrillator Patches", Pacing and Clinical Electrophysiology, Jan. 1993, Part II, vol. 16, 6 pages.
Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.
Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.
Bolling et al., "Automatic Internal Cardioverter Defibrillator: A Bridge to Heart Transplantation", Heart Lung Transplantation, Abstract Only, Jul.-Aug. 1991, 1 page.
Steinke et al., "Subepicardial Infarction, Myocardial Impression, and Ventricular Penetration by Sutureless Electrode and Leads", Chest; 70: 1, Jul. 1976, 2 pages.
Avogadros Lab Supply Inc., Catalog; Scoopula with Beech Wood Handle, can be found on-line at http://www.avogadro-lab-supply.com/search.php, accessed Oct. 6, 2013, 1 page.
Medtronic, Inc. 6996SQ Subcutaneous, Unipolar Lead with Defibrillation Coil Electrode, Technicial Manual, 1997, 22 pages.
Medtronic, Inc. 6996T Tunneling Tool, Technical Manual, 1997, 12 pages.
Pebax Product Brochure, 14 pages and can be found on-line at http://www.pebax.com/export/sites/pebax/.content/medias/downloads/literature/pebax-product-range-brochure.pdf. accessed on-line at the above address on Jul. 27, 2017, 14 pages.
Cigna et al., "A New Technique for Substernal Colon Transposition with a Breast Dissector: Report of 39 Cases", Journal of Plastic, Reconstructive and Aesthetic Surgery, 2006:59, 4 pages.
Tung et al., "Minimal Invasive Extra Cardiac Placement of High Voltage Defibrillator Leads", Poster 3; S200 Abstract, PO-3-4; St. Paul Hospital, Vancouver, British Columbia, Canada, 1 pages.
Molina et al, "An Epicardial Subxiphoid Implantable Defibrillator Lead: Superior Effectiveness After Failure of Standard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.
Baudoin et al., "The Superior Epigastric Artery Does Not Pass Through Larrey's Space (Trigonum Sternocostale)" Surgical Radiol Anat (2003), 25: 259-262.
Haydin et al., "Subxiphoid Approach to Epicardial Implantation of Implantable Cardioverter Defibrillators in Children", PACE, vol. 36, Aug. 2013, 5 pages.
Falk et al., "External Cardiac Pacing Using Low Impedance Electrodes Suitable for Defibrillation: A Comparative Blinded Study," Journal of American College of Cardiology, vol. 22, No. 5, Nov. 1, 1993, 5 pages.
Laudon, M. K., "Pulse Output", Chapter 11 of Design of Pacemakers, Published by the Institute of Electrical and Electronics Engineers, Inc., New York,(1995), 30 pages.
Ganapathy et al., "Implantable Device to Monitor Cardiac Activity with Sternal Wires," Pace, vol. 37, Dec. 2014, 11 pages.
Guenther et al., "Substernal Lead Implantation: A Novel Option to Manage DFT Failure in S-ICD patients," Clinical Research Cardiology, Published On-line Oct. 2, 2014, 3 pages.
Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.
Alexander et al., "Implications of Implantable Cardioverter Defibrillator Therapy in Congenital Heart Disease and Pediatrics", Journal of Cardiovascular Electrophysiology, vol. 15, No. 1, Jan. 2004, 5 pages.
Baddour et al., Update on Cardiovascular Implantable Electronic Device Infections and Their Management—A Scientific Statement From the American Heart Association, Circulation available at http://circ.ahajournals.org, Jan. 26, 2010; 23 pages.
Bauersfeld et al., "Initial Experience With Implantable Cardioverter Defibrillator Systems Using Epicardial and Pleural Electrodes in Pediatric Patients", The Annals of Thoracic Surgery, 2007, vol. 84, 3 pages.
Berul et al., "Minimally Invasive Cardioverter Defibrillator Implantation for Children: An Animal Model and Pediatric Case Report", Journal of Pacing and Clinical Electrophysiology, Dec. 2001, vol. 24, No. 12, 6 pages.
Hsia et al., "Novel Minimally Invasive, Intrapericardial Implantable Cardioverter Defibrillator Coil System: A Useful Approach to Arrhythmia Therapy in Children", The Annals of Thoracic Surgery, 2009, vol. 87, 6 pages.
Tung et al., Invention Disclosure Form for "Hybrid Endovascular and Extrvascular Implantable Cardioverter-Defibrillator System", Mar. 2006, 10 pages.
Cooper et al., "Implantable Cardioverter Defibrillator Lead Complications and Laser Extraction in Children and Young Adults With Congenital Heart Disease: Implications for Implantation and Management", Journal of Cardiovascular Electrophysiology, vol. 14, No. 4, Apr. 2003, 7 pages.
Advisory Action from U.S. Appl. No. 14/261,488, dated Dec. 26, 2018, 4 pp.
Final Office Action from U.S. Appl. No. 14/261,470, dated Dec. 3, 2018, 12 pp.
Final Office Action from U.S. Appl. No. 14/261,456, dated Nov. 8, 2018, 12 pp.
Advisory Action from U.S. Appl. No. 14/261,479, dated Jan. 22, 2019, 3 pp.
Response to Final Office Action dated Sep. 18, 2018, from U.S. Appl. No. 14/261,479, filed Nov. 19, 2018, 12 pp.
Prosecution History from U.S. Appl. No. 14/261,470, dated Apr. 28, 2016 through Jul. 17, 2019, 176 pp.
Prosecution History from U.S. Appl. No. 14/261,488, dated May 25, 2016 through Jul. 11, 2019, 208 pp.
Prosecution History from U.S. Appl. No. 14/261,456, dated May 25, 2016 through Jul. 17, 2019, 188 pp.
Prosecution History from U.S. Appl. No. 14/261,479, dated May 25, 2016 through Jul. 11, 2019, 182 pp.
Prosecution Hisotry from U.S. Appl. No. 14/261,460, dated May 13, 2016 through May 11, 2017, 29 pp.
Notice of Allowance from U.S. Appl. No. 14/261,470, dated Sep. 11, 2019, 5 pp.
Notice of Allowance from U.S. Appl. No. 14/261,456, dated Sep. 13, 2019, 5 pp.
Notice of Allowance from U.S. Appl. No. 14/261,479, dated Aug. 27, 2019, 5 pp.
Response to Office Action dated Jul. 11, 2019, from U.S. Appl. No. 14/261,488, filed Oct. 11, 2019, 19 pp.

* cited by examiner

IMPLANTABLE MEDICAL DEVICE SYSTEM HAVING IMPLANTABLE CARDIOVERTER-DEFIBRILLATOR (ICD) SYSTEM AND SUBSTERNAL LEADLESS PACING DEVICE

This application is a divisional of U.S. patent application Ser. No. 14/261,460 filed Apr. 25, 2014 (allowed and granting as U.S. Pat. No. 9,717,923), which claims the benefit of U.S. Provisional Application No. 61/819,946, filed on May 6, 2013, the content of each of which is incorporated herein by reference in their entirety.

FIELD OF THE INVENTION

The present application relates to methods and systems for providing an implantable medical cardiac defibrillation system having a substernal leadless pacing device.

BACKGROUND OF THE INVENTION

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter defibrillator (ICD) system has been shown to be beneficial at preventing SCD. An ICD system includes an ICD, which is a battery powered electrical shock device, that may include an electrical housing electrode (sometimes referred to as a can electrode), that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, subcutaneous ICD systems have been devised to provide shocks to the heart without placing electrical lead wires within the heart or attaching electrical wires directly to the heart.

Subcutaneous ICD systems have been devised to deliver shocks to the heart by the use of a defibrillation lead placed subcutaneously on the torso. However, the subcutaneous ICD systems may require an output of around 80 Joules (J) of energy to provide effective defibrillation therapy. As a result, subcutaneous ICDs may require larger batteries and more storage capacitors than transvenous ICDs. As such, the subcutaneous ICDs are generally larger in size than transvenous ICDs. The large size of the subcutaneous ICD may compromise patient comfort, decrease system longevity and/or increase cost of the system. In addition, conventional subcutaneous ICD systems are incapable of delivering anti-tachycardia pacing (ATP) without extreme discomfort to the patient, which is a standard therapy in transvenous ICDs to terminate lethal tachyarrhythmias without providing a shock.

SUMMARY OF THE INVENTION

The present application advantageously provides implantable cardiac systems and methods for providing substernal pacing in an implantable cardiac defibrillation system. In one embodiment, an implantable cardiac system comprises an implantable cardioverter-defibrillator (ICD) system and an implantable leadless pacing device communicatively coupled to the ICD. The ICD system includes an ICD implanted subcutaneously in a patient and an implantable defibrillation lead having a proximal portion coupled to the ICD and a distal portion having a defibrillation electrode configured to deliver a defibrillation shock to a heart of the patient. The leadless pacing device includes a housing, a first electrode on the housing, a second electrode on the housing, and a pulse generator within the housing and electrically coupled to the first electrode and the second electrode. The housing of the leadless pacing device is implanted substantially within an anterior mediastinum of the patient and the pulse generator is configured to deliver pacing pulses to a heart of the patient via a therapy vector formed between the first and second electrode.

In another embodiment, the disclosure is directed to a method of providing electrical stimulation therapy to a heart of a patient using an implantable cardioverter-defibrillator (ICD) system and an implantable leadless pacing device. The method comprises generating one or more pacing pulses with the implantable leadless pacing device, delivering the one or more pacing pulses via two electrodes on a housing of the leadless pacing device that is implanted substantially within an anterior mediastinum of the patient, generating a defibrillation pulse with the ICD system implanted within the patient, and delivering the defibrillation pulse via at least one electrode of a defibrillation lead of the ICD system.

In a further embodiment, an implantable cardiac system comprises an implantable cardioverter-defibrillator (ICD) system an implantable leadless pacing device communicatively coupled to the ICD. The ICD system includes an ICD implanted subcutaneously in a patient and an implantable defibrillation lead having a proximal portion coupled to the ICD and a distal portion having a defibrillation electrode configured to deliver a defibrillation shock to a heart of the patient and at least one pace electrode configured to deliver one or more pacing pulses to the heart of the patient. The leadless pacing device includes a housing, a first electrode on the housing, a second electrode on the housing, and a sensing module within the housing and electrically coupled to the first electrode and the second electrode. The housing is implanted substantially within an anterior mediastinum of the patient. The sensing module is configured to sense electrical signals of the heart of the patient via a sensing vector formed between the first and second electrodes.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1A:
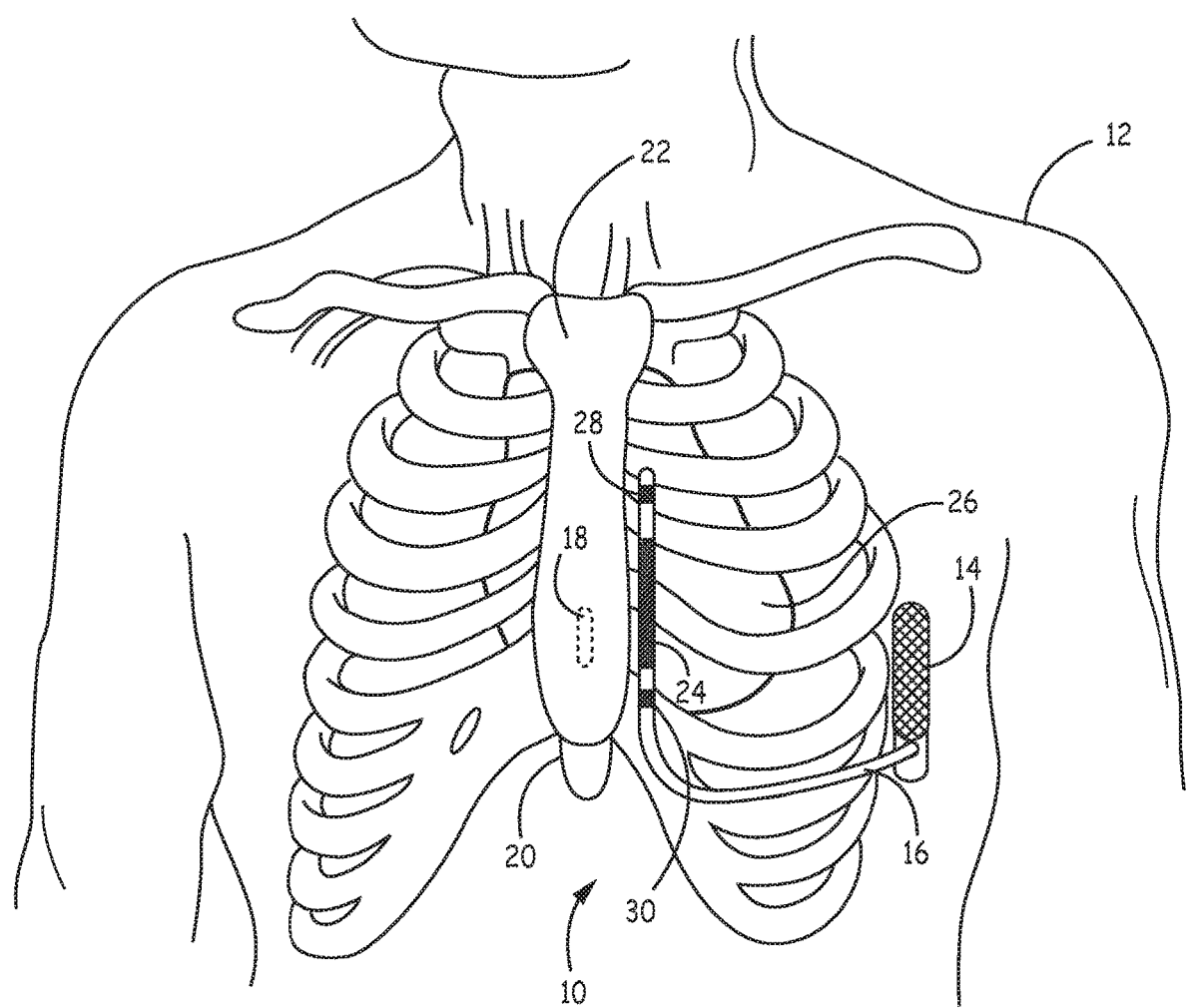
FIG. 1A is a front view of a patient implanted with and implantable cardiac system.
Figure 1B:
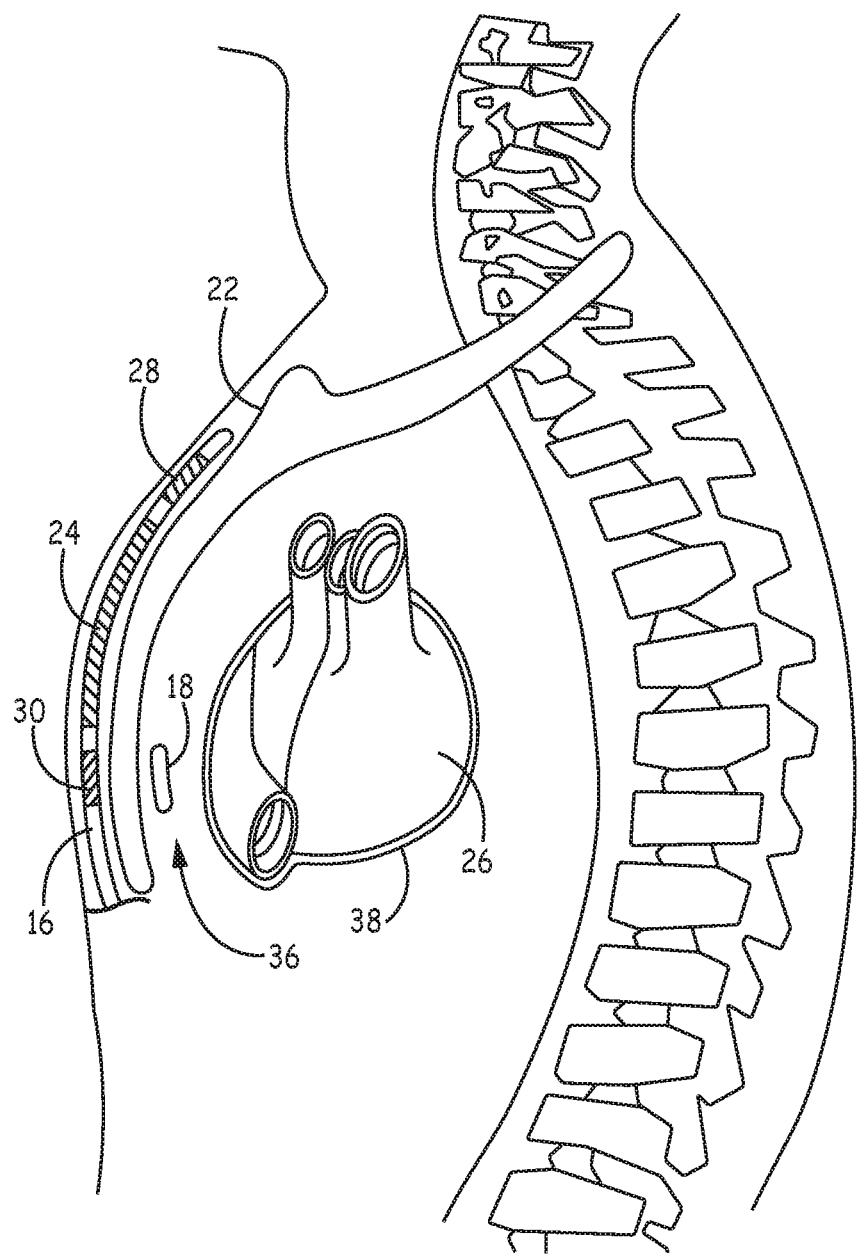
FIG. 1B is a side view of the patient with the implantable cardiac system.
Figure 1C:
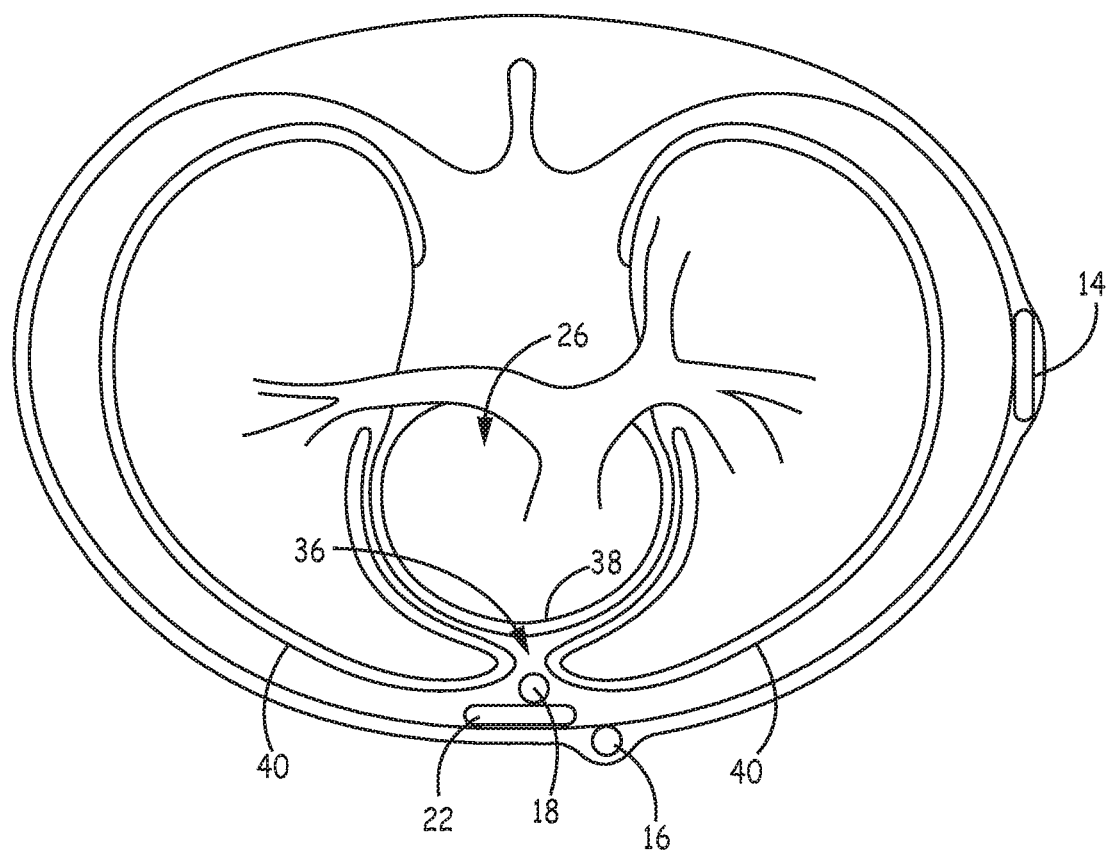
FIG. 1C is a transverse view of the patient with the implantable cardiac system.

FIGS. 1A-C are conceptual diagrams of an implantable cardiac system 10 implanted within a patient 12. FIG. 1A is a front view of patient 12 implanted with implantable cardiac system 10. FIG. 1B is a side view of patient 12 with implantable cardiac system 10. FIG. 1C is a transverse view of patient 12 with implantable cardiac system 10. FIGS. 1A-C are described in the context of implantable cardiac pacing. However, the techniques of this disclosure may also be used in the context of other implantable medical devices configured to provide electrical stimulation pulses to stimulate other organs, tissues, muscles, or nerves within the body of patient 12. For example, leadless IPG 10 implanted in the manner described herein may provide electrical stimulation therapy for neuro-cardiac applications and/or sleep apnea or respiration therapy.

Implantable cardiac system 10 includes an implantable medical device, in this example, an ICD 14 connected to a defibrillation lead 16. Implantable cardiac system 10 also includes a leadless implantable pulse generator (IPG) 18. In the example illustrated in FIGS. 1A-C, ICD 14 is implanted subcutaneously on the left midaxillary of patient 12 above the ribcage. ICD 14 may, however, be implanted at other subcutaneous locations on patient 12 as described later.

Defibrillation lead 16 includes an elongated lead body having a proximal end that includes a connector (not shown) configured to be connected to ICD 14 and a distal portion that includes electrodes 24, 28, and 30. Defibrillation lead 16 extends subcutaneously above the ribcage from ICD 14 toward a center of the torso of patient 12, e.g., toward xiphoid process 20 of patient 12. At a location near xiphoid process 20, defibrillation lead 16 bends or turns and extends superior subcutaneously above the ribcage and/or sternum, substantially parallel to sternum 22. Although illustrated in FIGS. 1A-C as being offset laterally from and extending substantially parallel to sternum 22, defibrillation lead 16 may be implanted at other locations, such as over sternum 22, offset to the right of sternum 22, angled lateral from sternum 22 at either the proximal or distal end, or the like.

Elongated lead body contains one or more elongated electrical conductors (not illustrated) that extend within the lead body from the connector at the proximal lead end to electrodes 24, 28, and 30 located along the distal portion of lead 16. The elongated lead body may have a generally uniform shape along the length of the lead body. In one example, the elongated lead body may have a generally tubular or cylindrical shape along the length of the lead body. In another example, the distal portion (or all of) the elongated lead body may have a flat, ribbon shape. The lead body of lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead body of lead 16 may engage with respective ones of electrodes 24, 28, and 30. In one example, each of electrodes 24, 28, and 30 is electrically coupled to a respective conductor within the lead body. The respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 24, 28, and 30 and transmit sensed electrical signals from one or more of electrodes 24, 28, and 30 to the sensing module within ICD 14.

Defibrillation lead 16 is placed along sternum 22 such that a therapy vector between defibrillation electrode 24 and a housing electrode of ICD 14 (or other second electrode of the therapy vector) is substantially across the ventricle(s) of heart 26. The therapy vector may, in one example, be viewed as a line that extends from a point on defibrillation electrode 24, e.g., center of defibrillation electrode 24, to a point on the housing electrode of ICD 14, e.g., center of the housing electrode. In one example, the therapy vector between defibrillation electrode 24 and the housing electrode of ICD 14 (or other second electrode of the therapy vector) is substantially across the right ventricle of heart 26.

Defibrillation electrode 24 is illustrated in FIG. 1 as being an elongated coil electrode. Defibrillation electrode 24 may vary in length depending on a number of variables. Defibrillation electrode 24 may, in one example, have a length of between approximately 5-10 centimeters (cm). However, defibrillation electrode 24 may have a length less than 5 cm and greater than 10 cm in other embodiments. Another example, defibrillation electrode 24 may have a length of approximately 2-16 cm.

In other embodiments, however, defibrillation electrode 24 may be a flat ribbon electrode, paddle electrode, braided or woven electrode, mesh electrode, segmented electrode, directional electrode, patch electrode or other type of electrode besides an elongated coil electrode. In one example, defibrillation electrode 24 may be formed of a first segment and a second segment separated by a distance and having at least one sensing electrode located between the first and second defibrillation electrode segments. In other embodiments, defibrillation lead 16 may include more than one defibrillation electrode. For example, the first and second segments described above may be coupled to different conductors within the lead body such that the first and second segments function as separate defibrillation electrodes along the distal portion of lead 16. As another example, defibrillation lead 16 may include a second defibrillation electrode (e.g., second elongated coil electrode) near a proximal end of lead 16 or near a middle portion of lead 16.

Defibrillation lead 16 also includes electrodes 28 and 30 located along the distal portion of defibrillation lead 16. In the example illustrated in FIGS. 1A-C, electrode 28 and 30 are separated from one another by defibrillation electrode 24. In other examples, however, electrodes 28 and 30 may be both distal of defibrillation electrode 24 or both proximal of defibrillation electrode 24. In instances in which defibrillation electrode 24 is a segmented electrode with two defibrillation segments, electrodes 28 and 30 may be located between the two segments. Alternatively, one of electrodes 28 and 30 may be located between the two segments with the other electrode located proximal or distal to defibrillation electrode 24. Electrodes 28 and 30 may comprise ring electrodes, short coil electrodes, hemispherical electrodes, segmented electrodes, directional electrodes, or the like. In other embodiments, defibrillation lead 16 may not include electrodes 28 and/or 30. In this case, defibrillation lead 16 would only include defibrillation electrode 24 and sensing may be achieved using electrodes of leadless IPG 18, as described further below. Alternatively, defibrillation lead 16 may include more than two sensing electrodes.

ICD 14 may obtain sensed electrical signals corresponding with electrical activity of heart 26 via a combination of sensing vectors that include combinations of electrodes 28 and/or 30 and the housing electrode of ICD 14. For example, ICD 14 may obtain electrical signals sensed using a sensing vector between electrodes 28 and 30, obtain electrical signals sensed using a sensing vector between electrode 28 and the conductive housing electrode of ICD 14, obtain electrical signals sensed using a sensing vector between electrode 30 and the conductive housing electrode of ICD 14, or a combination thereof. In some instances, ICD 14 may even obtain sensed electrical signals using a sensing vector that includes defibrillation electrode 24.

Lead 16 may further include one or more anchoring mechanisms that are positioned along the length of the lead body. The anchoring mechanisms may affix lead 16 to reduce movement of lead 16 from its desired subcutaneous location. For example, the lead 16 may be anchored at one or more locations situated between the distal end and a point along the length of the portion of the lead body at or near the incision/entry site. The one or more anchoring mechanism (s) may either engage fascia, muscle or tissue of patient 12 or may simply be wedged therein to affix the lead subcutaneously to prevent excessive motion or dislodgment. The anchoring mechanisms may be integrated into the lead body. In alternative embodiments, the anchoring mechanisms may be discrete elements formed in line with the lead body. In addition or alternatively, the lead may be anchored through a suture that fixedly-secures the lead to the patient's musculature, tissue or bone at the xiphoid entry site. In some embodiments, the suture may be sewn through pre-formed suture holes to the patient.

Leadless IPG 18 is implanted underneath/below sternum 22 substantially within anterior mediastinum 36. Anterior mediastinum 36 may be viewed as being bounded laterally by pleurae 40, posteriorly by pericardium 38, and anteriorly by sternum 22. In some instances, the anterior wall of anterior mediastinum 38 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, leadless IPG 18 may be implanted substantially within the loose connective tissue and/or substernal musculature of anterior mediastinum 36. A leadless IPG implanted substantially within anterior mediastinum 36 will be referred to herein as a substernal leadless IPG. Also, electrical stimulation, such as pacing, provided by a leadless IPG implanted substantially within anterior mediastinum 36 will be referred to herein as substernal electrical stimulation or substernal pacing.

Leadless IPG 18 includes a housing 31 having electrodes 32 and 34. Leadless IPG 18 may be implanted substantially within anterior mediastinum 36 such that leadless IPG 18 can sense electrical activity of heart 26 and/or deliver electrical stimulation, e.g., pacing, to heart 26 via electrodes 32 and 34. In one example, leadless IPG 18 may be implanted such that electrodes 32 and 34 are located substantially over a cardiac silhouette of one or both ventricles as observed via an anterior-posterior (AP) fluoroscopic view of heart 26. In another example leadless IPG 18 may be implanted such that a bipolar therapy vector between electrodes 32 and 34 is centered or otherwise located over the ventricle(s). However, leadless IPG 18 may be positioned at other locations as long as the bipolar therapy vector between electrodes 32 and 34 result in capture of the ventricle(s) of heart 26.

In the example illustrated in FIGS. 1A-C, leadless IPG 18 is located substantially centered under sternum 22. In other instances, however, leadless IPG 18 may be implanted such that it is offset laterally from the center of sternum 22. In some instances, leadless IPG 18 may extend laterally enough such that all or a portion of leadless IPG 18 is underneath/below the ribcage in addition to or instead of sternum 22.

Although leadless IPG 18 is described herein as being implanted substantially within anterior mediastinum 36, leadless IPG 18 may be implanted in other non-vascular, extra-pericardial locations, including the gap, tissue, or other anatomical features around the perimeter of, and adjacent to, the pericardium but not attached to heart 26 and not above sternum 22 or ribcage. For example, leadless IPG 18 may be implanted within the "substernal space" defined by the undersurface between the sternum and the body cavity but not including the pericardium. The substernal space may alternatively be referred to by the terms "retrosternal space" or "mediastinum" or "infrasternal" as is known to those skilled in the art and includes the anterior mediastinum 36. The substernal space may also include the anatomical region described in Baudoin, Y. P., et al., entitled "The superior epigastric artery does not pass through Larrey's space (trigonum sternocostale)." Surg. Radiol. Anat. 25.3-4 (2003): 259-62 as Larrey's space. In other words, leadless IPG 18 may be implanted in the region around the outer surface of heart 26, but not attached to heart 26.

Leadless IPG 18 may be communicatively coupled to ICD 14. Leadless IPG 18 and ICD 14 may, for example, both include a communication module via which the devices exchange information via wireless communications. The information may include sensed electrical signals, detected cardiac events, e.g., detected VT or VF episodes, therapy information, or the like. Leadless IPG 18 and ICD 14 may, for example, be coupled via inductive coupling, RF coupling, tissue conductance communication, or other wireless communication mechanism. Leadless IPG 18 may communicate with ICD 14 to communicate ICD 14 may analyze the sensed electrical signals from one or more of the sensing vectors of defibrillation lead 16 or from electrical signals sensed by leadless IPG 18 and communicated to ICD 14 to detect tachycardia, such as ventricular tachycardia (VT) or ventricular fibrillation (VF). In response to detecting the tachycardia, ICD 14 may communicate with leadless IPG 18 to initiate one or more ATP therapies in an attempt to terminate the tachycardia without delivering a defibrillation shock. If the one or more ATP therapies are not successful or it is determined that ATP therapy is not desired, ICD 14 may deliver one or more defibrillation or cardioversion shocks via defibrillation electrode 24 of defibrillation lead 16. ICD 14 and leadless IPG 18 may coordinate therapy in a number of manners. Various techniques for coordinating therapy between an ICD 14 and leadless IPG 18 are described in co-pending patent application Ser. No. 13/756,085, filed Jan. 31, 2013 and titled, "SYSTEMS AND METHODS FOR LEADLESS PACING AND SHOCK THERAPY," which is incorporated herein by reference in its entirety.

Leadless IPG 18 may also analyze the sensed electrical signals via electrodes 32 and 34 of leadless IPG 18 to detect tachycardia, such as ventricular tachycardia or ventricular fibrillation. In some instances, leadless IPG 18 delivers one or more ATP therapies via electrodes 32 and 34 in response to detecting the tachycardia in an attempt to terminate the tachycardia without delivering a defibrillation shock. In other instances, leadless IPG 18 may not deliver ATP therapy until it receives a communication from ICD 14 indicating detection of tachycardia by ICD 14. If the one or more ATP therapies are not successful (as determined by ICD 14, leadless IPG 18, or both) or it is determined that ATP therapy is not desired, ICD 14 may deliver one or more defibrillation shocks via defibrillation electrode 24 of defibrillation lead 16. In some instances, the electrical signals sensed by leadless IPG 18 may be communicated to ICD 14 for analysis or vice versa. In this manner, ICD 14 and leadless IPG 18 coordinate with one another to provide pacing therapies including, but not limited to ATP therapy or post shock pacing. For example, leadless IPG 18 may provide ATP pacing, post shock pacing, bradycardia pacing or other pacing in coordination with ICD 14. In still further instances, leadless IPG 18 may provide ATP pacing while ICD 14 provides post-shock pacing.

In other instances, leadless IPG 18 may be a sense-only device and may be used for VT/VF discrimination and detection to improve the defibrillation and/or cardioversion therapy provided by ICD 14. In this case, leadless IPG 18 may communicate the sensed data and/or any VT/VF detections to ICD 14. Moreover, in such an example, ICD 14 may be configured to provide any pacing therapies (e.g., ATP and/or post-shock pacing) in addition to the defibrillation or cardioversion therapies in an attempt to terminate the tachyarrhythmia.

Figure 2:
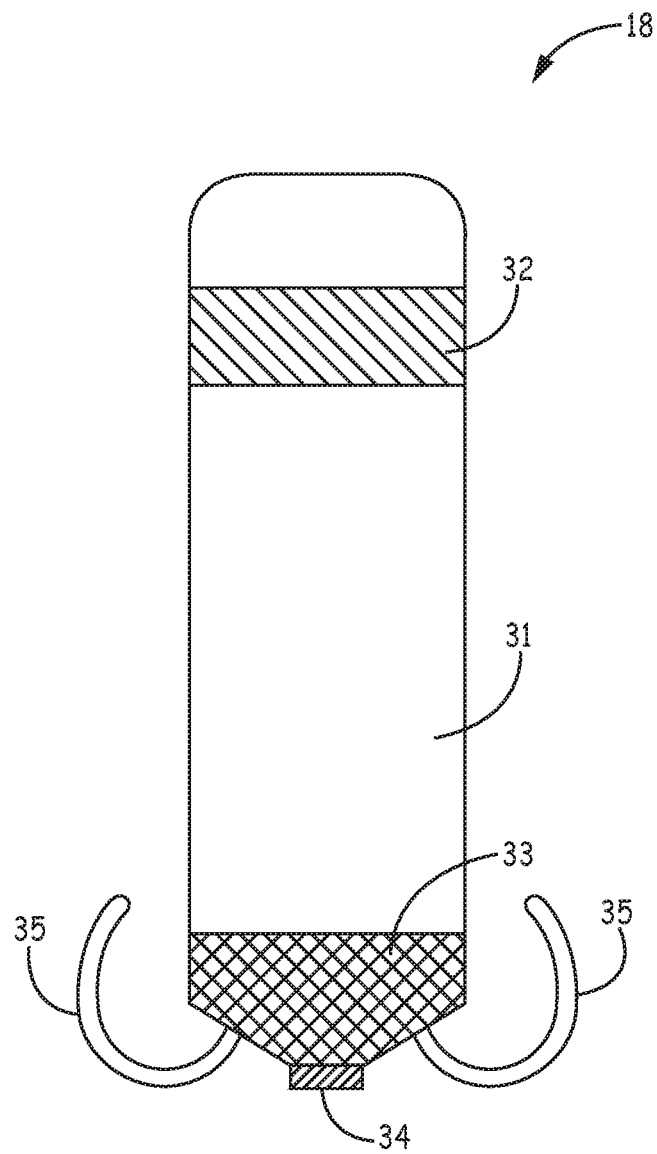
FIG. 2 illustrates a conceptual view of an example leadless implantable pulse generator in further detail.

An example leadless IPG 18 is illustrated in further detail in FIG. 2. As illustrated in FIG. 2, leadless IPG 18 includes a housing 31, electrodes 32 and 34 coupled to housing 31 or formed by housing 31, a non-conductive spacer 33 and a fixation mechanism (e.g., tines 35 of FIG. 2) to attach leadless IPG 18 at a desired location within anterior mediastinum 36. Leadless IPG 18 may have other fixation mechanisms in addition to or instead of tines 35.

Housing 31 forms a hermetic seal that protects components of leadless IPG 18. As will be described in further detail herein, housing 31 may protect one or more processors, memories, transmitters, receivers, sensors, sensing circuitry, therapy circuitry, power sources, and other appropriate components. Housing 31 may take on any of a number of shapes. In the example illustrated in FIG. 2, housing 31 is generally cylindrical or pill-shaped. In another example, housing 14 may be more of flat, rectangular shape. Housing 31 may have any of a number of dimensions. In one example, housing 31 may be less than approximately 30 mm in length and be less than or equal to 20 French. In other examples, housing 14 may be larger than 30 mm in length such that electrodes on the housing may be located over both the atria and the ventricles.

Housing 31 of may be substantially formed of a conductive material, such as a medical grade stainless steel, titanium alloy, or other metal or metal alloy. Housing 31 also includes an insulative layer formed over at least a portion of housing 31, such as a layer of parylene, polyimide, or urethane. In some examples, electrodes 32 and 34 may be defined by uninsulated portions of an outward facing portion of housing 31. Housing 31 also includes a non-conductive spacer 33 that separates the portion of housing forming electrode 32 from the portion of housing forming electrode 34. Other division between insulated and uninsulated portions of housing 31 may be employed to define a different number or configuration of housing electrodes. In other instances, electrode 32 and/or 34 may be otherwise coupled to housing 31.

Electrodes 32 and 34 are illustrated in FIG. 2 as a tip electrode and ring or cylindrical electrode, respectively, disposed on the exterior surface of housing 31. In one example, electrodes 32 and 34 may each have surface areas between approximately 2-55 mm$^2$. In another example, one or both of electrodes 16 and 18 may have surface areas up to 200 mm$^2$. Electrode 32 and electrode 34 may have an electrode spacing of between approximately 5-30 mm. In other instances, such as when multi-chamber sensing or pacing is desired, housing 31 may be much longer, e.g., up to 20 or 30 cm, and the electrode spacing may be up to 16 cm. Electrode 32 may be used as a cathode and electrode 34 may be used as an anode, or vice versa, for delivering electrical stimulation therapy to and/or sensing electrical signals associated with heart 26. In other examples, electrode 32 and/or 34 may be formed in other shapes, such as a hemispherical electrode that includes one of the ends of housing 31 or that does not extend around the entire circumference of housing 31.

In some instances, electrodes 32 and 34 or housing 31 of leadless IPG 18 may be shaped, oriented, designed or otherwise configured to reduce extra-cardiac stimulation. For example, electrodes 32 and 34 or housing 31 may be shaped, oriented, designed or otherwise configured to focus, direct or point electrodes 32 and 34 toward heart 26. In this manner, pacing pulses delivered by leadless IPG 18 are directed toward heart 26 and not outward toward skeletal muscle. For example, electrodes 32 or 34 or housing 31 may be partially coated or masked with a polymer (e.g., polyurethane) or another coating material (e.g., tantalum pentoxide) on one side or in different regions so as to direct the pacing signal toward heart 26 and not outward toward skeletal muscle.

Leadless IPG 18 of this disclosure may take on various other configurations. For example, leadless IPG 18 of this disclosure may conform with the leadless IPG illustrated and described in FIG. 2 and paragraphs [0029][0033] of copending U.S. patent application Ser. No. 14/261,488, entitled "SUBSTERNAL LEADLESS ELECTRICAL STIMULATION SYSTEM," filed on the same day as the current application. The content of the referenced portions of that application are incorporated herein by reference in their entirety.

Leadless IPG 18 may analyze the sensed electrical signals of heart 26 obtained from electrodes 32 and 34 to detect cardiac events, e.g., tachycardia. Leadless IPG 18 also provides pacing pulses to heart 26 via electrodes 32 and 34. Leadless IPG 18 may be configured to generate and deliver the pacing pulses to provide anti-tachycardia pacing (ATP), bradycardia pacing, post shock pacing, or other pacing therapies or combination of pacing therapies. In one example, leadless IPG 18 may generate and deliver ATP therapy in response to detecting ventricular tachycardia. In another example, leadless IPG 18 may generate and deliver ATP therapy in response to receiving a communication from ICD 14 indicating that ICD 14 detected ventricular tachycardia. In another example, leadless IPG 18 may detect delivery of a defibrillation or cardioversion shock and provide post-shock pacing in response to detecting delivery of the shock. In this manner, ATP therapy (or other pacing therapy) may be provided in a subcutaneous ICD system without entering the vasculature or the pericardium.

The configuration described above in FIGS. 1A-1C is directed to providing ventricular pacing via leadless IPG 18. In situations in which atrial pacing is desired in addition to or instead of ventricular pacing, leadless IPG 18 may be positioned further superior. In some instances, more than one leadless pacing devices 18 may be utilized for dual chamber pacing, e.g., with one leadless IPG 18 providing atrial pacing and the other leadless IPG 18 providing ventricle pacing. Alternatively, leadless IPG 18 may be positioned over the ventricle and include a small tether extending up to the atrium with an electrode on the tether. Leadless IPG 18 could sense and/or pace via the electrode on the tether. As another alternative, leadless IPG 18 could be elongated to serve this purpose under the sternum, so that there are one or more electrodes on the housing that senses/paces the atrium and one or more electrodes on the housing that senses/paces ventricle. In yet further embodiments, leadless IPG 18 may be used in combination with a pacing lead implanted substernally to provide dual chamber pacing.

The examples illustrated in FIGS. 1A-C are exemplary in nature and should not be considered limiting of the techniques described in this disclosure. In other examples, ICD 14 and defibrillation lead 16 may be implanted at other locations. For example, ICD 14 may be implanted in a subcutaneous pocket in the right chest. In this example, defibrillation lead 16 may be extend subcutaneously from the device toward the manubrium of the sternum and bend or turn and extend inferior subcutaneously from the manubrium of the sternum, substantially parallel with the sternum.

In another embodiment contemplated herein, the system 10 of FIG. 1 may include more than one leadless IPG. In a further embodiment contemplated herein, the system 10 of FIG. 1 may have defibrillation lead 16 implanted at least partially in the anterior mediastinum. In this case, both the distal portion of defibrillation lead 16 and leadless IPG 18 would be located substantially within the anterior mediastinum. Defibrillation lead 16 may extend subcutaneously from ICD 14 toward xiphoid process 20, and at a location near xiphoid process 20 bends or turns and extends superior underneath/below the sternum, e.g., along the posterior side of the sternum. In this manner, system 10 may be configured to deliver both substernal defibrillation therapy and substernal pacing therapy to patient 12. In other instances, defibrillation lead 16 and/or leadless IPG 18 may be implanted in other non-vascular, extra-pericardial locations, including the gap, tissue, or other anatomical features around the perimeter of, and adjacent to, the pericardium but not attached to the heart and not above the sternum or ribcage. In other words, lead 16 may be implanted in the region around the outer surface of heart 26, but not attached to heart 26. Placing defibrillation lead 16 in this location may reduce the energy required to defibrillate heart 26, which may reduce the power consumed by ICD 14. This may increase the longevity of the ICD 14, decrease the size of ICD 14, or both.

In the example illustrated in FIG. 1, system 10 includes an ICD system that provides pacing, but the techniques may be applicable to other cardiac systems, including cardiac resynchronization therapy defibrillator (CRT-D) systems, cardioverter systems, or combinations thereof. For example, leadless IPG 18 may be configured to provide electrical stimulation pulses to stimulate nerves, skeletal muscles, diaphragmatic muscles, e.g., for various neuro-cardiac applications and/or for apnea or respiration therapy.

In addition, it should be noted that system 10 may not be limited to treatment of a human patient. In alternative examples, system 10 may be implemented in non-human patients, e.g., primates, canines, equines, pigs, ovines and felines. These other animals may undergo clinical or research therapies that may benefit from the subject matter of this disclosure.

Figure 3:
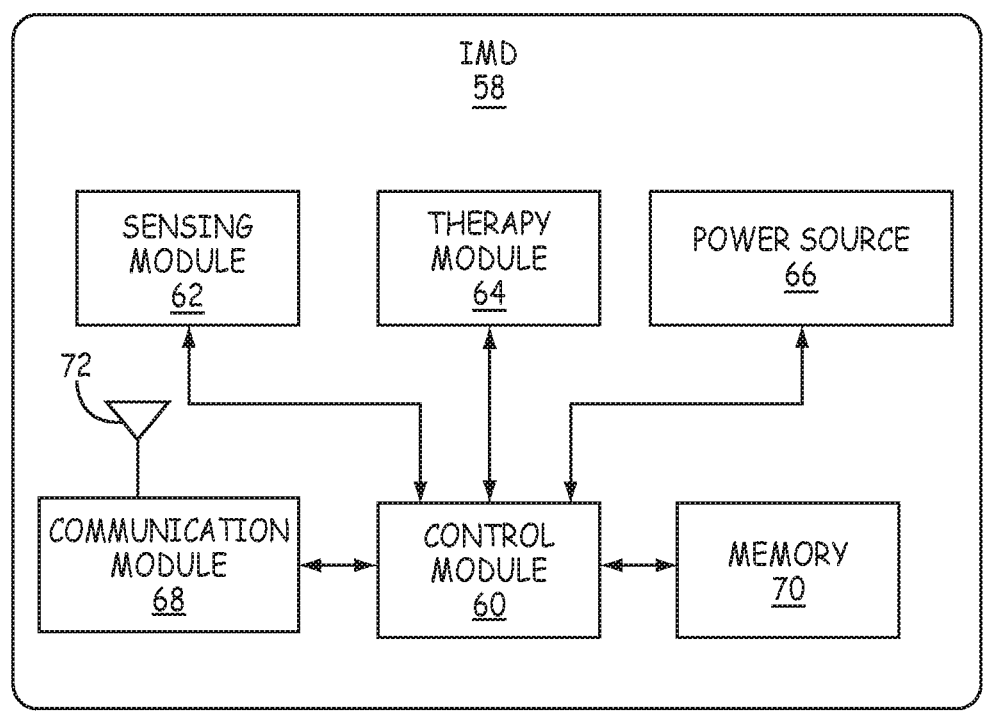
FIG. 3 is a functional block diagram of an example configuration of electronic components of an example implantable medical device.

FIG. 3 is a functional block diagram of an example configuration of electronic components of an example implantable medical device (IMD) 58, such as either ICD 14 or leadless IPG 18. IMD 58 includes a control module 60, sensing module 62, therapy module 64, communication module 68, and memory 70. The electronic components may receive power from a power source 66, which may be a rechargeable or non-rechargeable battery. In other embodiments, IMD 58 may include more or fewer electronic components. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Sensing module 62 is electrically coupled to some or all of the electrodes of the associated device or lead coupled to the device. In the case of ICD 14, for example, sensing module 62 is electrically coupled to some or all of electrodes 24, 28, and 30 via the conductors of lead 16 and one or more electrical feedthroughs or to the housing electrode via conductors internal to the housing of ICD 14. In the case of leadless IPG 18, sensing module 62 is electrically coupled to electrodes 32 and 34 via conductors internal to the housing of leadless IPG 18.

Sensing module 62 is configured to obtain electrical signals sensed via one or more combinations of electrodes and process the obtained signals. The components of sensing module 62 may be analog components, digital components or a combination thereof. Sensing module 62 may, for example, include one or more sense amplifiers, filters, rectifiers, threshold detectors, analog-to-digital converters (ADCs) or the like. Sensing module 62 may convert the sensed signals to digital form and provide the digital signals to control module 60 for processing or analysis. For example, sensing module 62 may amplify signals from the sensing electrodes and convert the amplified signals to multi-bit digital signals by an ADC. Sensing module 62 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to control module 60.

Control module 60 may process the signals from sensing module 62 to monitor electrical activity of heart 26 of patient 12. Additionally or alternatively, control module 60 may process signals sensed by another device to monitor electrical activity of heart 26 of patient 12 in addition to or instead of signals sensed by its own electrodes. For example, leadless IPG 18 may send electrical signals sensed by electrodes 32 and 34 to ICD 14 or ICD 14 may send electrical signals sensed by electrodes 24, 28, and 30 to leadless IPG 18. Control module 60 may store signals obtained by sensing module 62 or received by another device as well as any generated EGM waveforms, marker channel data or other data derived based on the sensed signals or received by another device in memory 70. Control module 60 may analyze the EGM waveforms and/or marker channel data to detect cardiac events (e.g., VT or VF).

Therapy module 64 is configured to generate and deliver electrical stimulation therapy to heart 26. Therapy module 64 may include one or more pulse generators, capacitors, and/or other components capable of generating and/or storing energy to deliver as pacing therapy, defibrillation therapy, cardioversion therapy, cardiac resynchronization therapy, other therapy or a combination of therapies depending on the type of IMD. In response to detecting the cardiac event (e.g., VT or VF), control module 60 may control therapy module 64 to deliver the desired therapy to treat the cardiac event. In the case of ICD 14, for example, therapy module 64 may generate and deliver cardioversion or defibrillation shocks via defibrillation electrode 24. In the case of leadless IPG 18, therapy module 64 may generate and delivery ATP therapy via electrodes 32 and 34. In other instances, therapy module 64 may generate and deliver other therapies, including post shock pacing or bradycardia pacing.

Control module 60 may control therapy module 64 to generate and deliver the electrical stimulation therapy to heart 26 via one or more therapy vectors using combinations of electrodes of the associated device or lead coupled to the device or using electrodes of two or more devices/leads. Control module 60 controls therapy module 64 to generate electrical stimulation therapy with the amplitudes, pulse widths, timing, frequencies, electrode combinations or electrode configurations specified by a selected therapy program.

In the case of pacing therapy provided by leadless IPG 18, e.g., ATP, post-shock pacing, and/or bradycardia pacing, control module 60 controls therapy module 64 to generate and deliver pacing pulses with any of a number of amplitudes, pulse widths, or other characteristic to capture heart 26. For example, the pacing pulses may be monophasic, biphasic, or multi-phasic (e.g., more than two phases). The pacing thresholds of heart 26 when delivering pacing pulses from the anterior mediastinum using leadless IPG 18 may depend upon a number of factors, including location, type, size, orientation, and/or spacing of electrodes 32 and 34, physical abnormalities of heart 26 (e.g., pericardial adhesions or myocardial infarctions), or other factor(s).

The increased distance from electrodes 32 and 34 to the heart tissue may result in heart 26 having increased pacing thresholds compared to transvenous pacing thresholds. To this end, therapy module 64 may be configured to generate and deliver pacing pulses having larger amplitudes and/or pulse widths than conventionally required to obtain capture via transvenously implanted lead or a lead attached to heart 26. In one example, therapy module 64 may generate and deliver pacing pulses having amplitudes of less than or equal to 8 volts and pulse widths between 0.5-3.0 milliseconds. In another example, therapy module 64 may generate and deliver pacing pluses having amplitudes of between 5 and 10 volts and pulse widths between approximately 3.0 milliseconds and 10.0 milliseconds. In another example, pulse widths of the pacing pulses may be between approximately 2.0 milliseconds and 8.0 milliseconds. In a further example, therapy module 64 may generate and deliver pacing pluses having pulse widths between approximately 0.5 milliseconds and 20.0 milliseconds. In another example, therapy module 64 may generate and deliver pacing pluses having pulse widths between approximately 1.5 milliseconds and 20.0 milliseconds.

In some cases, therapy module 64 may generate pacing pulses having longer pulse durations than conventional transvenous pacing pulses to achieve lower energy consumption. For example, therapy module 64 may be configured to generate and deliver pacing pulses having pulse widths or durations of greater than two (2) milliseconds. In another example, therapy module 64 may be configured to generate and deliver pacing pulses having pulse widths or durations greater than two (2) milliseconds and less than or equal to three (3) milliseconds. In another example, therapy module 64 may be configured to generate and deliver pacing pulses having pulse widths or durations of greater than or equal to three (3) milliseconds. In another example, therapy module 64 may be configured to generate and deliver pacing pulses having pulse widths or durations of greater than or equal to five (5) milliseconds. In another example, therapy module 64 may be configured to generate and deliver pacing pulses having pulse widths or durations of greater than or equal to ten (10) milliseconds. In a further example, therapy module 64 may be configured to generate and deliver pacing pulses having pulse widths between approximately 3-10 milliseconds. In a further example, therapy module 64 may be configured to generate and deliver pacing pulses having pulse widths or durations of greater than or equal to fifteen (15) milliseconds. In yet another example, therapy module 64 may be configured to generate and deliver pacing pulses having pulse widths or durations of greater than or equal to twenty (20) milliseconds.

Depending on the pulse widths, leadless IPG 18 may configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. Typically the lower amplitudes require longer pacing widths as illustrated in the experimental results. Reducing the amplitude of pacing pulses delivered by leadless IPG 18 may reduce the likelihood of extra-cardiac stimulation. Some experimental results are provided later illustrating some example combinations of pacing amplitudes and widths obtained using pacing leads. However, such results may be applicable to leadless IPGs as well.

In the case of defibrillation therapy, e.g., defibrillation shocks provided by defibrillation electrode 24 of defibrillation lead 16, control module 60 controls therapy module 64 to generate defibrillation shocks having any of a number of waveform properties, including leading-edge voltage, tilt, delivered energy, pulse phases, and the like. Therapy module 64 may, for instance, generate monophasic, biphasic or multiphasic waveforms. Additionally, therapy module 64 may generate defibrillation waveforms having different amounts of energy. For example, therapy module 64 may generate defibrillation waveforms that deliver a total of between approximately 60-80 Joules (J) of energy for subcutaneous defibrillation. Therapy module 64 may also generate defibrillation waveforms having different tilts. In the case of a biphasic defibrillation waveform, therapy module 64 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide subcutaneous defibrillation via defibrillation electrode 24.

Communication module 68 includes any suitable hardware, firmware, software or any combination thereof for communicating with another device, such as a clinician programmer, a patient monitoring device, or the like. For example, communication module 68 may include appropriate modulation, demodulation, frequency conversion, filtering, and amplifier components for transmission and reception of data with the aid of antenna 72. Antenna 72 may be located within connector block of IMD 58 or within housing IMD 58. Example communication techniques include RF telemetry, inductive telemetry, tissue conductance communication, or other technique.

ICD 14 and leadless IPG 18 may communicate one or more of sensed electrical signals, detection of a cardiac event (including VT or VF), delivery of a therapy, outcome of the delivery of the therapy, indication of therapy about to be delivered, parameters of the therapy provided, or other information, via communication module 68 as described above with respect to FIGS. 1A-C.

The various modules of IMD 58 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 70 may include computer-readable instructions that, when executed by control module 60 or other component of IMD 58, cause one or more components of IMD 58 to perform various functions attributed to those components in this disclosure. Memory 70 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 4:
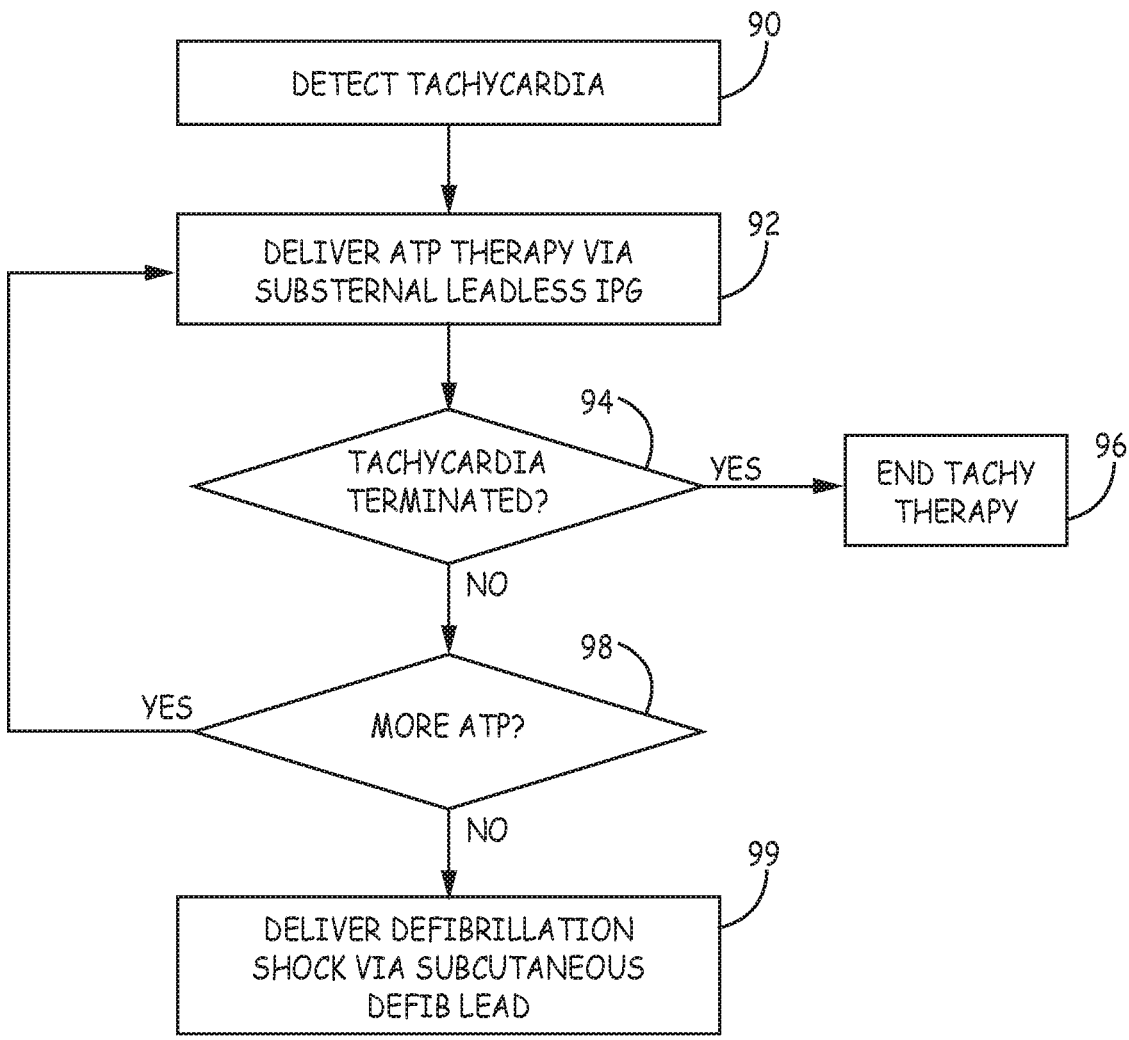
FIG. 4 is a flow diagram illustrating example operation of an implantable cardiac system in accordance with this disclosure.

FIG. 4 is a flow diagram illustrating example operation of an implantable cardiac system, such as implantable cardiac system 10 of FIGS. 1A-1C. Initially, ICD 14 and/or leadless IPG 18 analyze sensed electrical signals to detect tachycardia, such as ventricular tachycardia or ventricular fibrillation (90). As described above, ICD 14 may analyze electrical signals obtained via electrodes 24, 28, and 30 of lead 16 and/or sensed electrical signals obtained via electrodes 32 and 34 of leadless IPG 18 and wirelessly communicated to ICD 14. Likewise, leadless IPG 18 may analyze electrical signals obtained via electrodes 32 and 34 of leadless IPG 18 and/or sensed electrical signals obtained via electrodes 24, 28, and 30 of lead 16 and wirelessly communicated to leadless IPG 18 by ICD 14.

In response to ICD 14 and/or leadless IPG 18 detecting tachycardia, leadless IPG 18 may deliver one or more sequence of ATP via electrodes 32 and 34, which are implanted substantially within anterior mediastinum 36 (92). In one example, leadless IPG 18 may detect the tachycardia and begin delivering ATP in response to the detection. In another example, leadless IPG 18 may not begin delivering ATP until it receives a communication from ICD 14 indicating that tachycardia has been detected. As described above, the pacing pulses provided by leadless IPG 18 may, in some instances, have longer pulse widths than conventional pacing pulses. For example, leadless IPG 18 may be configured to deliver pacing pulses having pulse widths of greater than two milliseconds. In other instances, leadless IPG 18 may be configured to deliver pacing pulses having pulse widths of between three and ten milliseconds. Other ranges of pulse widths, as well as pacing amplitudes, rates, number of pulses, and the like and various combinations of characteristics are described in further detail above. In some instances, leadless IPG 18 may be configured to only deliver ATP to particular types of tachycardia. Leadless IPG 18 may, for example, distinguish between VT and VF and only provide ATP in instances in which the tachycardia is VT. If the tachycardia is VF, the leadless IPG 18 may be configured to not provide ATP.

After delivery of the sequence of ATP, leadless IPG 18 determines whether the tachycardia is terminated (94). Leadless IPG 18 may, for example, analyze the most recent sensed activity of the heart to determine if the sequence of ATP terminated the tachycardia. In another example, leadless IPG 18 may determine that the tachycardia is terminated in response to receiving a communication from ICD 14 with such an indication. When leadless IPG 18 determines that the tachycardia has terminated ("YES" branch of block 94), leadless IPG 18 ends the ATP and returns to analyzing sensed electrical signals (96).

When leadless IPG 18 determines that the tachycardia has not terminated ("NO" branch of block 94), leadless IPG 18 determines whether additional sequences of ATP pacing pulses will be provided (98). Leadless IPG 18 may, for example, be configured to deliver ATP therapy that consists of two or more sequences of ATP pacing pulses. When leadless IPG 18 determines that additional sequences of ATP pacing pulses will be provided ("YES" branch of block 98), leadless IPG 18 delivers a second sequence of ATP pacing pulses via electrodes 32 and 34 implanted substantially within anterior mediastinum 36 (92). The second sequence of pacing pulses may be the same as the first sequence. Alternatively, the second sequence of pacing pulses may be different than the first sequence. For example, the ATP pulses of the first and second sequences of pulses may have one or more different characteristics including, but not limited to, different pacing amplitudes, pulse widths, rates, therapy vectors, and/or variation among pacing pulses.

When no additional sequences of ATP pacing pulses will be provided ("NO" branch of block 98), ICD 14 delivers a defibrillation pulse via a therapy vector that includes defibrillation electrode 24 of defibrillation lead 16 (99). As described above, leadless IPG 18 may communicate to ICD 14 that no additional ATP therapy will be provided. As described with respect to FIGS. 1A-1C, defibrillation lead 16 may, in some instances, be implanted subcutaneously above the sternum and/or ribcage. Alternatively, defibrillation lead 16 may be implanted such that the distal portion of lead 16 including electrodes 24, 28, and 30 are substantially within anterior mediastinum 36. The amount of energy of the defibrillation pulse will depend on the location of the defibrillation electrode 24.

Experiments

Three acute procedures were performed using pigs, with the animals in a dorsal recumbency. An incision was made near the xiphoid process and a Model 4194 lead was delivered to the substernal/retrosternal space using a 6996T tunneling tool and sheath. An active can emulator (ACE) was placed in a subcutaneous pocket on either the right chest (first acute experiment) or the left midaxillary (second and third acute experiments). Various pacing configurations were tried and different pieces of equipment were used as the source of stimulation. Multiple pulse widths were used in delivering the pacing pulse. Across experiments, several different substernal/retrosternal lead electrode locations were utilized.

In the second and third experiments the impact of lead location on electrical performance was investigated by moving the lead to several locations under the sternum and collecting data to generate strength-duration curves at each location.

In all three acute experiments, the substernal/retrosternal lead was placed and electrical data collected. The lead was moved intentionally many times across experiments to better understand the location best suited to capturing the heart at low pacing thresholds, with different locations and parameters tried until pacing capability was gained and lost. A range of thresholds based on location and pacing configuration was recorded. For this reason, the lowest threshold result for each acute experiment is reported, as are strength-duration curves showing the range of pacing values obtained from suitable pacing locations. In all cases, it was determined that positioning the substernal/retrosternal pacing electrode approximately over the ventricle of the cardiac silhouette provided best results.

Experiment 1

In the first acute study, a Medtronic Attain bipolar OTW 4194 lead was implanted substernally/retrosternally, and two active can emulators were positioned, one in the right dorsal lateral region (ACE1) and one on the right midaxillary (ACE2). The 4194 lead was placed directly below the sternum, in the mediastinum, with the lead tip and body running parallel to the length of the sternum. Various pacing configurations were tried and electrical data collected.

The smallest threshold observed was 0.8 volts, obtained when pacing from the tip of the substernal/retrosternal 4194 lead to ACE1 (10 ms pulse width and Frederick Heir instrument as the source of stimulation). It was possible to capture using a smaller pulse width, though threshold increased as the pulse width shortened (1.5V at 2 ms in this same configuration with a bp isolater, made by FHC product #74-65-7, referred to herein as "Frederick Heir Stimulator."). Many additional low thresholds (1-2 volts) were obtained with different pacing configurations and pulse durations.

Figure 5:
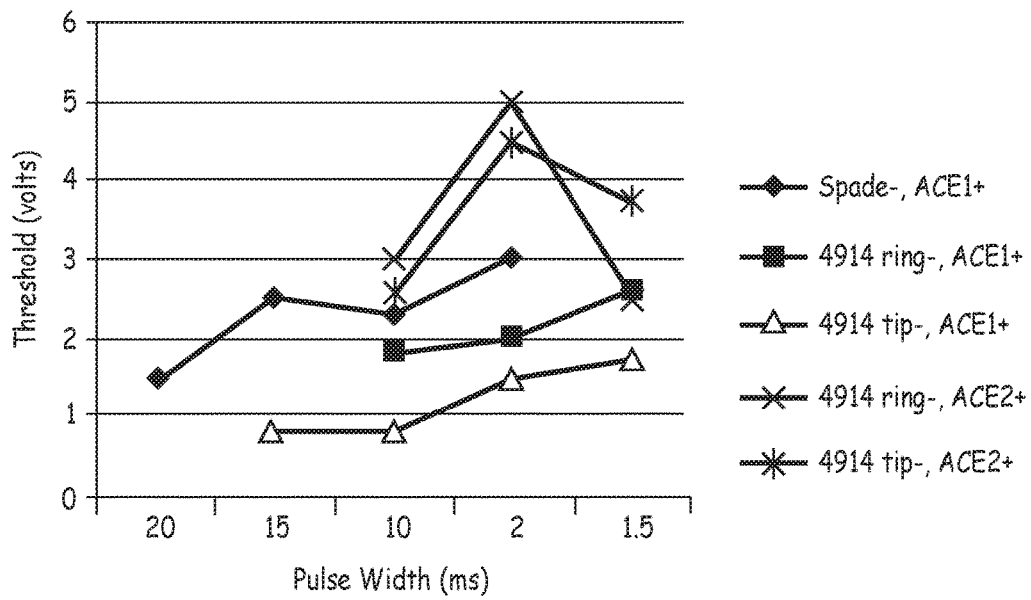
FIG. 5 is a graph illustrating strength-duration curves showing the capture thresholds obtained at various pulse widths during a first acute study.

FIG. 5 illustrates a strength-duration curve showing the capture thresholds obtained at various pulse widths during the first acute study. Note that all configurations paced from either the tip or the ring of the substernally/retrosternally implanted 4194 lead (−) to one of the two active can emulators (+). In one instance, a large spade electrode (instead of a Model 4194 lead) was used as the substernal/retrosternal electrode, as noted in the legend of FIG. 1.

As shown, several pacing configurations and parameters were tried. Across the configurations reported in the graph above, threshold values ranged from 0.8 volts to 5.0 volts, with threshold generally increasing as pulse width was shortened. In a few instances, the threshold at 1.5 ms pulse width was smaller than the threshold at 2.0 ms. It should be noted that the threshold value obtained at 1.5 ms was always recorded using the Medtronic 2290 analyzer as the stimulation source, whereas all other threshold measurements for the first acute experiment (at pulse widths of 2, 10, 15 and 20 ms) were obtained using a Frederick Heir instrument as the source of stimulation. Differences in these two instruments may account for the difference in threshold values at similar pulse widths (1.5 ms and 2 ms).

In general, the first acute experiment demonstrated the feasibility of substernal/retrosternal pacing by producing small capture thresholds (average=2.5±1.2 volts), using several different pacing configurations and parameters.

Experiment 2

A second acute experiment was conducted. In the second acute, however, the animal presented with pericardial adhesions to the sternum. Because of the pericardial adhesion, the ventricular surface of the cardiac silhouette was rotated away from the sternum—an anatomical difference that may have resulted in higher thresholds throughout this experiment.

As in the previous acute experiment, a Model 4194 lead was placed under the sternum. An active can emulator was placed on the left midaxillary. The tip to ring section of the 4194 was positioned over the cardiac silhouette of the ventricle, as observed by fluoroscopy, and this position is notated "Position A" on the strength-duration graph illustrated in FIG. 6. The lead eventually migrated a very short distance closer to the xiphoid process during stimulation (still under the sternum) to reach "Position B," and additional electrical measurements were obtained successfully from this position as well.

The smallest threshold observed in the second acute experiment was 7V, obtained when pacing from the substernal/retrosternal 4194 ring electrode (−) to an ACE (+) on the left midaxillary in the first lead position (5 ms, 15 ms and 20 ms pulse widths, Frederick Heir stimulator). Additionally, thresholds of 8 and 9 volts were obtained with the lead in the second anatomical position, both from 4194 tip to ACE (unipolar) and 4194 tip to ring (bipolar) configurations at multiple pulse widths. The two lines that appear to run off the chart were instances of no capture.

Figure 6:
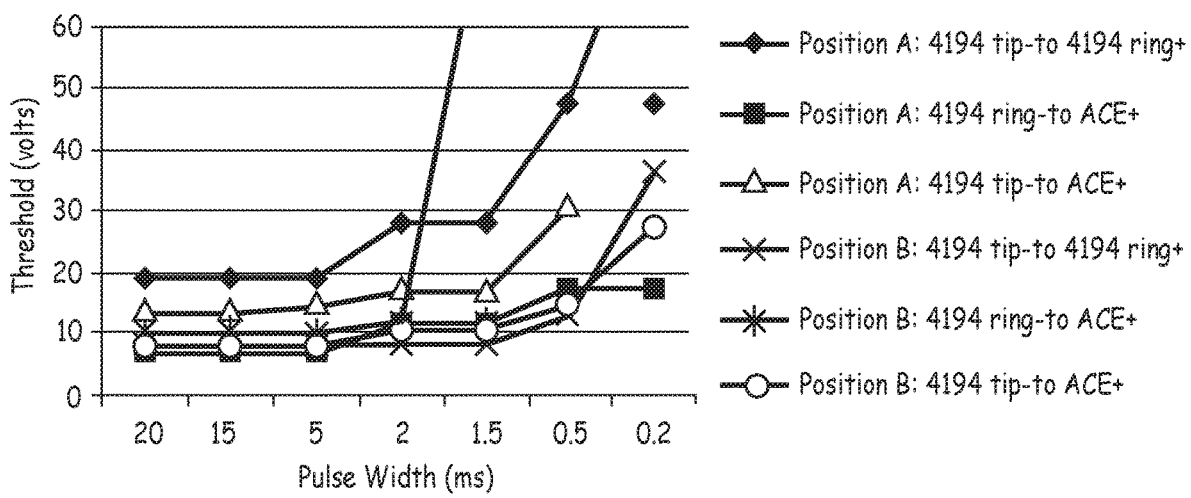
FIG. 6 is a graph illustrating strength-duration curves showing the capture thresholds obtained at various pulse widths during a second acute study.

All of the electrical values reported in FIG. 6 were collected with the Frederick Heir instrument as the stimulation source. Extracardiac stimulation was observed with many of the electrical measurements obtained in a unipolar pacing configuration. No obvious extracardiac stimulation was observed when pacing in a bipolar configuration (4194 tip to ring), though a low level of stimulation could be felt with a hand on the animal's chest.

Experiment 3

A third and final acute experiment was conducted demonstrating the feasibility of substernal/retrosternal pacing. As in the previous two acute experiments, a 4194 lead was placed under the sternum. An active can emulator was placed on the left midaxillary. In this experiment, the substernal/retrosternal 4194 lead was intentionally positioned so that the lead tip was initially near the second rib, far above the cardiac silhouette of the ventricle. The lead tip was then pulled back (toward the xiphoid process) one rib space at a time, collecting electrical data at each position. As in previous experiments, low capture thresholds were obtained when the pacing electrodes were approximately positioned over the ventricular surface of the cardiac silhouette, as observed via fluoroscopy. When the lead tip was not over the ventricular surface of the cardiac silhouette, "no capture" was often the result.

As in previous experiments, pacing was performed from either the tip or the ring of the substernal/retrosternal 4194 lead (−) to the ACE (+) on the left midaxillary. However, in this acute experiment, a subcutaneous ICD lead was also positioned in its subcutaneous arrangement (as illustrated and described in FIGS. 1A-C). In some instances, the pacing configuration was from either the tip or the ring of the substernal/retrosternal 4194 lead (−) to either the ring or the coil of the subcutaneous ICD lead (+), so that the ICD lead and not the ACE was the indifferent electrode.

The smallest threshold observed across the experiment was 0.8V, obtained when pacing from the substernal/retrosternal 4194 tip electrode (−) to an ACE (+) on the left midaxillary when the lead was positioned such that the lead tip electrode was approximately under the sixth rib (20 ms pulse width and Frederick Heir stimulator). Many additional low thresholds were obtained with different pacing configurations, shorter pulse durations and different lead positions, again demonstrating the feasibility of substernal/retrosternal pacing. Obvious extracardiac stimulation generally was not observed with lower threshold measurements (at longer pulse durations) but was observed at higher thresholds.

Figure 7:
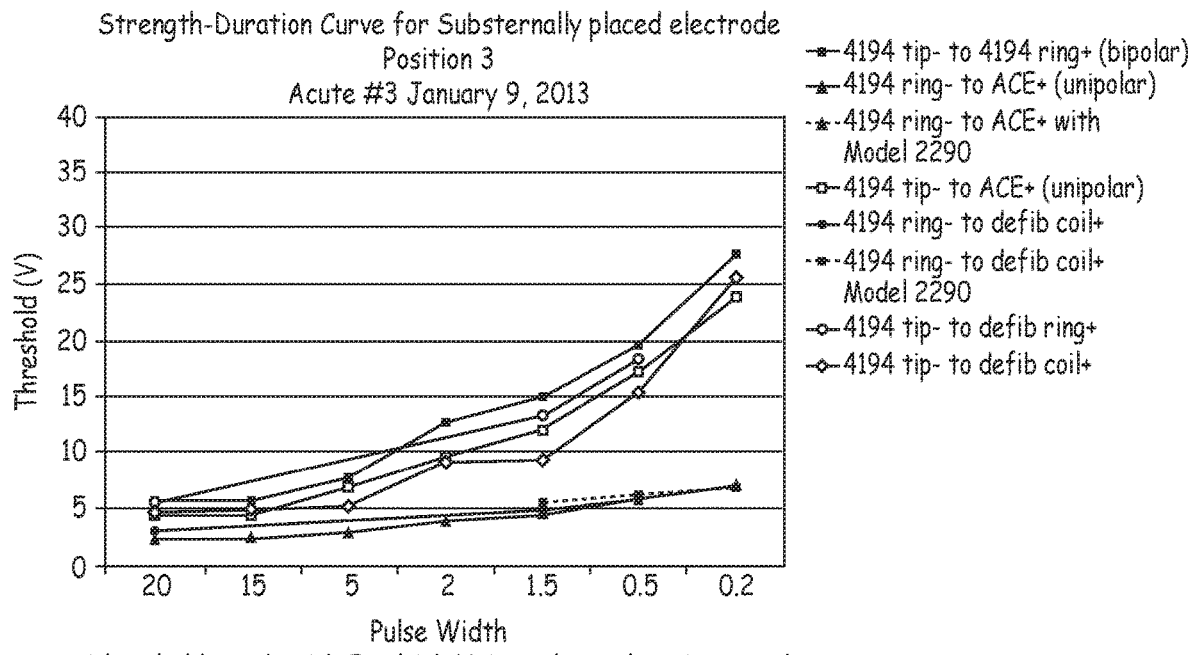
FIG. 7 is a graph illustrating strength-duration curves of electrical data from a third acute experiment with a lead positioned under the sternum in a first location.
Figure 8:
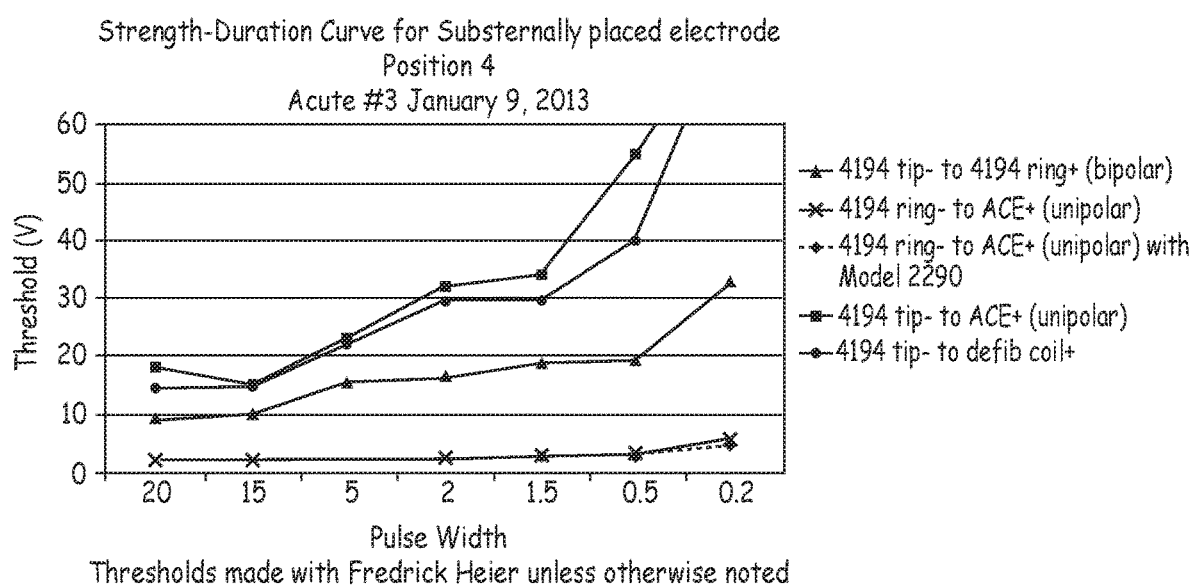
FIG. 8 is a graph illustrating strength-duration curves of electrical data from the third acute experiment with a lead positioned under the sternum in a second location.
Figure 9:
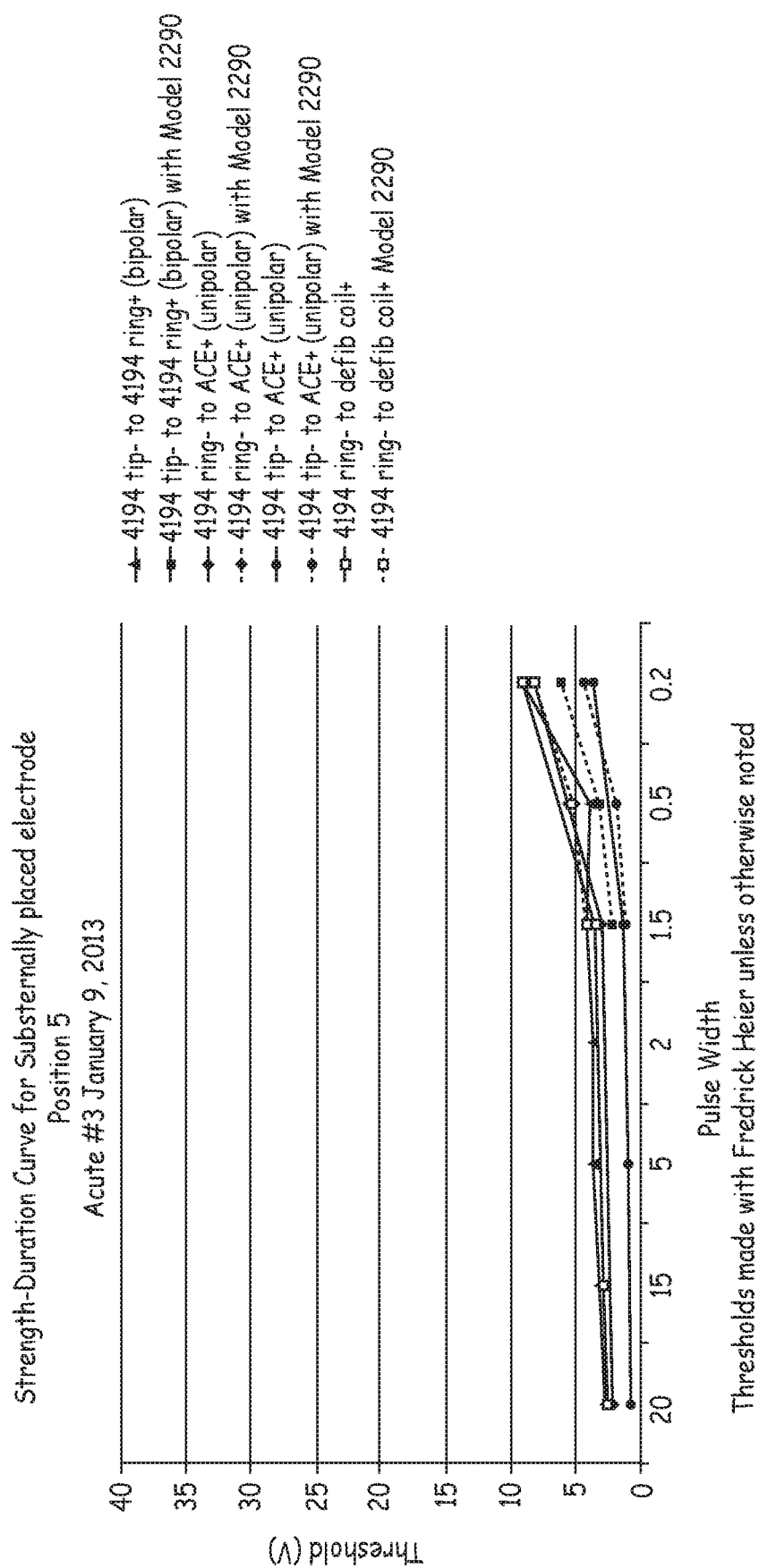
FIG. 9 is a graph illustrating strength-duration curves of electrical data from a third acute experiment with a lead positioned under the sternum in a third location.

The strength duration curves for lead positions 3-5 are presented in FIGS. 7-9, with individual graphs for each location due to the breadth of electrical data collected. Measurements made with the 2290 analyzer as the source of stimulation are noted. Other electrical measurements were made with the Frederick Heir instrument as the stimulation source.

FIG. 7 illustrates the strength-duration curve of electrical data from the third acute experiment when the 4194 lead tip was positioned under the sternum near the location of the $4^{th}$ rib. Several therapy vectors resulted in low pacing thresholds, generally when pulse widths were quite long. At shorter pulse widths, threshold increased.

FIG. 8 illustrates the strength-duration curve of electrical data from the third acute experiment when the 4194 lead tip was positioned under the sternum near the location of the $5^{th}$ rib. The two lines that appear to run off the chart at 0.2 ms were instances of no capture. FIG. 8 demonstrates the position dependence of the substernal/retrosternal lead. Thresholds were higher overall in this anatomical location (the lead tip near the $5^{th}$ rib), though capture was still possible and in the 4194 ring (−) to ACE (+) configuration, moderately low (2 volts at 20 ms). There generally was no significant extracardiac stimulation observed except with pulse widths of 0.2 ms and 0.5 ms in the 4194 tip (−) to ACE (+) configuration and in the unipolar configuration going from the 4194 tip (−) to the coil of the subcutaneous ICD lead at pulse widths of 1.5 ms and shorter, all of which resulted in the highest recorded threshold readings in this lead position.

FIG. 9 illustrates the strength-duration curve of electrical data from the third acute experiment when the 4194 lead tip was positioned under the sternum near the location of the $6^{th}$ rib. FIG. 9 shows the position dependence of the substernal/retrosternal electrode. When the pacing electrode is optimally located over the ventricular surface of the cardiac silhouette (as observed via fluoroscopy), pacing threshold is low. Low thresholds were very repeatable in this anatomical location, even at shorter pulse durations and in many different pacing configurations. Extracardiac stimulation generally was not apparent at low thresholds and longer pulse durations throughout this experiment.

All three acute experiments demonstrated the feasibility of pacing from a substernal/retrosternal electrode location. The lowest threshold results across the three acute procedures were 0.8 volts, 7 volts and 0.8 volts, respectively, with the second acute procedure involving an anatomical difference (pericardial adhesions) that tipped the ventricular surface of the heart away from its normal orientation with the sternum, resulting in higher pacing thresholds. However, for the purposes of anti-tachycardia pacing, conventional devices typically default to maximum output (8V at 1.5 ms) for ATP therapy delivery. Given this, even the 7V threshold obtained in the second acute experiment could be satisfactory for ATP therapy.

The ability to capture the heart at low pacing thresholds was dependent upon electrode position. As observed through these experiments, the substernal/retrosternal pacing electrode provide the best outcomes when positioned approximately over the ventricular surface of the cardiac silhouette, which is easily observed via fluoroscopy and encompasses a reasonably large target area for lead placement. In the third acute experiment, for example, capture was achieved at three separate positions, with the lead tip at approximately ribs 4, 5 and 6, all of which were near the ventricular surface of the cardiac silhouette.

Pacing thresholds increased with shorter pulse durations. In many instances, however, low pacing thresholds were obtained even at short pulse widths, especially when the substernal/retrosternal pacing electrode was positioned over the ventricular surface of the cardiac silhouette. In other instances, longer pulse durations (10-20 ms) were necessary to obtain capture or to achieve lower capture thresholds.

Across experiments, it was possible to pace from the substernal/retrosternal lead to an active can emulator positioned near the animal's side (unipolar) and also from the substernal/retrosternal lead to a subcutaneous ICD lead (unipolar). If a subcutaneous ICD system incorporated a pacing lead, placed substernally/retrosternally, for the purpose of anti-tachycardia pacing, both of the aforementioned unipolar pacing configurations would be available for a physician to choose from.

These experiments also demonstrated the ability to pace in a bipolar configuration entirely under the sternum (4194 tip (−) to 4194 ring (+), substernally/retrosternally), indicating that either a bipolar lead positioned under the sternum might be used for anti-tachycardia pacing purposes.

Overall, the results of these acute experiments demonstrate the ability to pace the heart from a substernal/retrosternal location, with the lead not entering the vasculature or the pericardial space, nor making intimate contact with the heart. The low threshold values obtained when pacing from a substernal/retrosternal lead location in these acute experiments suggest that pain-free pacing for the purpose of anti-tachycardia pacing in a subcutaneous ICD system is within reach.

Various examples have been described. These and other examples are within the scope of the following claims.

The invention claimed is:
1. A method of providing electrical stimulation therapy to a heart of a patient using an implantable cardioverter-defibrillator (ICD) system and an implantable leadless pacing device, the method comprising:
generating one or more pacing pulses with the implantable leadless pacing device;
delivering the one or more pacing pulses via two electrodes on a housing of the leadless pacing device implanted substantially within an anterior mediastinum of the patient such that the two electrodes on the housing are physically isolated from a pericardium of the patient;

generating a defibrillation pulse with an ICD of the ICD system implanted within a patient; and delivering the defibrillation pulse via at least one electrode of a defibrillation lead coupled to the ICD.

2. The method of claim 1, further comprising:
detecting, with the ICD, a ventricular tachycardia;
sending a communication from the ICD to the leadless pacing device to indicate the detection of the ventricular tachycardia by the ICD; and
generating and delivering the one or more pacing pulses in response to receiving the communication from the ICD.

3. The method of claim 2, further comprising:
sensing, with the leadless pacing device, electrical signals corresponding to cardiac activity of the heart of the patient using a sensing vector between a first electrode of the two electrodes on the housing of the leadless pacing device and a second electrode of the two electrodes on the housing of the leadless pacing device;
analyzing the sensed electrical signals to detect the ventricular tachycardia; and
generating and delivering the one or more pacing pulses in response to the analysis.

4. The method of claim 1, further comprising:
sensing, with the leadless pacing device, electrical signals corresponding to cardiac activity of the heart of the patient using a sensing vector between a first electrode of the two electrodes on the housing of the leadless pacing device and a second electrode of the two electrodes on the housing of the leadless pacing device;
analyzing the sensed electrical signals to detect one of a ventricular tachycardia and a ventricular fibrillation; and
generating and delivering the one or more pacing pulses in response to the analysis.

5. The method of claim 1, wherein generating and delivering the one or more pacing pulses comprises generating and delivering one or more pacing pulses having pulse amplitudes between approximately one (1) and twenty (20) volts.

6. The method of claim 1, wherein a distal portion of the defibrillation lead is implanted substantially within the anterior mediastinum such that a therapy vector from the electrode to the ICD is substantially across the ventricles of the heart.

7. The method of claim 1, wherein a distal portion of the defibrillation lead is implanted subcutaneously and superficial to a ribcage of the patient.

8. The method of claim 1, further comprising:
receiving, by the ICD from the leadless pacing device, a communication that includes at least one of electrical signals sensed by the leadless pacing device or tachyarrhythmia detections made by the leadless pacing device; and
utilizing, by the ICD, the at least one of the electrical signals sensed by the leadless pacing device or tachyarrhythmia detections made by the leadless pacing device to make a tachyarrhythmia detection.

9. The method of claim 1, further comprising delivering, with the ICD, post-shock pacing pulses to the heart using the at least one electrode of the defibrillation lead.

10. The method of claim 1, wherein generating and delivering the one or more pacing pulses comprises generating and delivering one or more pacing pulses having pulse widths between approximately one and a half (1.5) milliseconds and twenty (20) milliseconds.

11. The method of claim 10, wherein generating and delivering the one or more pacing pulses comprises generating and delivering one or more pacing pulses having pulse amplitudes between approximately one (1) and twenty (20) volts.

12. The method of claim 10, wherein generating and delivering the one or more pacing pulses comprises generating and delivering one or more pacing pulses having pulse widths greater than two (2) milliseconds and less than eight (8) milliseconds.

13. The method of claim 1, wherein delivering the one or more pacing pulses comprises delivering one or more pacing pulses having pulse amplitudes less than approximately two (2) volts.

* * * * *